(12) United States Patent
Urbanski

(10) Patent No.: US 12,005,202 B2
(45) Date of Patent: Jun. 11, 2024

(54) CATHETER HAVING TISSUE-ENGAGING DEVICE

(71) Applicant: Boston Scientific Medical Device Limited, Ballybrit (IE)

(72) Inventor: John Paul Urbanski, Toronto (CA)

(73) Assignee: Boston Scientific Medical Device Limited, Ballybrit (IE)

( * ) Notice: Subject to any disclaimer, the term of this patent is extended or adjusted under 35 U.S.C. 154(b) by 255 days.

(21) Appl. No.: 17/393,487

(22) Filed: Aug. 4, 2021

(65) Prior Publication Data

US 2022/0040451 A1 Feb. 10, 2022

Related U.S. Application Data

(60) Provisional application No. 63/062,511, filed on Aug. 7, 2020.

(51) Int. Cl.
*A61M 25/01* (2006.01)
*A61M 25/06* (2006.01)

(52) U.S. Cl.
CPC ........ *A61M 25/0138* (2013.01); *A61M 25/06* (2013.01); *A61M 2205/0216* (2013.01); *A61M 2210/122* (2013.01); *A61M 2210/125* (2013.01)

(58) Field of Classification Search
None
See application file for complete search history.

(56) References Cited

U.S. PATENT DOCUMENTS

| | | |
|---|---|---|
| 175,254 A | 3/1876 | Oberly |
| 827,626 A | 7/1906 | Gillet |
| 848,711 A | 4/1907 | Weaver |
| 1,072,954 A | 9/1913 | Junn |
| 1,279,654 A | 9/1918 | Charlesworth |
| 1,918,094 A | 7/1933 | Geekas |
| 1,996,986 A | 4/1935 | Weinberg |
| 2,021,989 A | 11/1935 | De Master |
| 2,146,636 A | 2/1939 | Lipchow |
| 3,429,574 A | 2/1969 | Williams |
| 3,448,739 A | 6/1969 | Stark et al. |
| 3,575,415 A | 4/1971 | Fulp et al. |
| 3,595,239 A | 7/1971 | Petersen |
| 4,129,129 A | 12/1978 | Amrine |
| 4,164,943 A * | 8/1979 | Hill ........................ A61M 25/02 604/174 |
| 4,244,362 A | 1/1981 | Anderson |
| 4,281,659 A * | 8/1981 | Farrar .................. A61B 5/1482 600/351 |
| 4,401,124 A | 8/1983 | Guess et al. |
| 4,639,252 A | 1/1987 | Kelly et al. |
| 4,641,649 A | 2/1987 | Walinsky et al. |

(Continued)

*Primary Examiner* — Manuel A Mendez
(74) *Attorney, Agent, or Firm* — Nelson Mullins Riley & Scarborough LLP

(57) ABSTRACT

An elongated catheter includes a tissue-engaging device configured to be urged to move and contact a first surface of the first biological wall. The tissue-engaging device extends from the distal catheter section. The tissue-engaging device is configured to be urged to puncture through the first biological wall. The tissue-engaging device is also configured to be urged to contact the first biological wall without impinging the second biological wall, after the tissue-engaging device has punctured through the first biological wall.

18 Claims, 7 Drawing Sheets

(56) References Cited

U.S. PATENT DOCUMENTS

| | | |
|---|---|---|
| 4,669,467 A | 6/1987 | Willett et al. |
| 4,682,596 A | 7/1987 | Bales et al. |
| 4,790,311 A | 12/1988 | Ruiz |
| 4,790,809 A | 12/1988 | Kuntz |
| 4,793,350 A | 12/1988 | Mar et al. |
| 4,807,620 A | 2/1989 | Strul et al. |
| 4,832,048 A | 5/1989 | Cohen |
| 4,840,622 A | 6/1989 | Hardy |
| 4,863,441 A | 9/1989 | Lindsay et al. |
| 4,884,567 A | 12/1989 | Elliott et al. |
| 4,892,104 A | 1/1990 | Ito et al. |
| 4,896,671 A | 1/1990 | Cunningham et al. |
| 4,928,693 A | 5/1990 | Goodin et al. |
| 4,936,281 A | 6/1990 | Stasz |
| 4,960,410 A | 10/1990 | Pinchuk |
| 4,977,897 A | 12/1990 | Hurwitz |
| 4,998,933 A | 3/1991 | Eggers et al. |
| 5,006,119 A | 4/1991 | Acker et al. |
| 5,019,076 A | 5/1991 | Yamanashi et al. |
| 5,047,026 A | 9/1991 | Rydell |
| 5,081,997 A | 1/1992 | Bosley et al. |
| 5,098,431 A | 3/1992 | Rydell |
| 5,112,048 A | 5/1992 | Kienle |
| 5,154,724 A | 10/1992 | Andrews |
| 5,201,756 A | 4/1993 | Horzewski et al. |
| 5,209,741 A | 5/1993 | Spaeth |
| 5,211,183 A | 5/1993 | Wilson |
| 5,221,256 A | 6/1993 | Mahurkar |
| 5,230,349 A | 7/1993 | Langberg |
| 5,281,216 A | 1/1994 | Klicek |
| 5,300,068 A | 4/1994 | Rosar et al. |
| 5,300,069 A | 4/1994 | Hunsberger et al. |
| 5,314,418 A | 5/1994 | Takano et al. |
| 5,318,525 A | 6/1994 | West et al. |
| 5,327,905 A | 7/1994 | Avitall |
| 5,364,393 A | 11/1994 | Auth et al. |
| 5,372,596 A | 12/1994 | Klicek et al. |
| 5,380,304 A | 1/1995 | Parker |
| 5,397,304 A | 3/1995 | Truckai |
| 5,403,338 A | 4/1995 | Milo |
| 5,423,809 A | 6/1995 | Klicek |
| 5,425,382 A | 6/1995 | Golden et al. |
| 5,490,859 A | 2/1996 | Mische et al. |
| 5,497,774 A | 3/1996 | Swartz et al. |
| 5,507,751 A | 4/1996 | Goode et al. |
| 5,509,411 A | 4/1996 | Littmann et al. |
| 5,540,681 A | 7/1996 | Strul et al. |
| 5,545,200 A | 8/1996 | West et al. |
| 5,555,618 A | 9/1996 | Winkler |
| 5,571,088 A | 11/1996 | Lennox et al. |
| 5,575,766 A | 11/1996 | Swartz et al. |
| 5,575,772 A | 11/1996 | Lennox |
| 5,599,347 A | 2/1997 | Hart et al. |
| 5,605,162 A | 2/1997 | Mirzaee et al. |
| 5,617,878 A | 4/1997 | Taheri |
| 5,622,169 A | 4/1997 | Golden et al. |
| 5,624,430 A | 4/1997 | Eton et al. |
| 5,667,488 A | 9/1997 | Lundquist et al. |
| 5,673,695 A | 10/1997 | Mcgee et al. |
| 5,674,208 A | 10/1997 | Berg et al. |
| 5,683,366 A | 11/1997 | Eggers et al. |
| 5,720,744 A | 2/1998 | Eggleston et al. |
| 5,741,249 A | 4/1998 | Moss et al. |
| 5,766,135 A | 6/1998 | Terwilliger |
| 5,779,688 A | 7/1998 | Imran et al. |
| 5,810,764 A | 9/1998 | Eggers et al. |
| 5,814,028 A | 9/1998 | Swartz et al. |
| 5,830,214 A | 11/1998 | Flom et al. |
| 5,836,875 A | 11/1998 | Webster, Jr. |
| 5,849,011 A | 12/1998 | Jones et al. |
| 5,851,210 A | 12/1998 | Torossian |
| 5,885,227 A | 3/1999 | Finlayson |
| 5,888,201 A | 3/1999 | Stinson et al. |
| 5,893,848 A | 4/1999 | Negus et al. |
| 5,893,885 A | 4/1999 | Webster, Jr. |
| 5,904,679 A | 5/1999 | Clayman |
| 5,916,210 A | 6/1999 | Winston |
| 5,921,957 A | 7/1999 | Killion et al. |
| 5,931,818 A | 8/1999 | Werp et al. |
| 5,944,023 A | 8/1999 | Johnson et al. |
| 5,951,482 A | 9/1999 | Winston et al. |
| 5,957,842 A | 9/1999 | Littmann et al. |
| 5,964,757 A | 10/1999 | Ponzi |
| 5,967,976 A | 10/1999 | Larsen et al. |
| 5,989,276 A | 11/1999 | Houser et al. |
| 6,007,555 A | 12/1999 | Devine |
| 6,009,877 A | 1/2000 | Edwards |
| 6,013,072 A | 1/2000 | Winston et al. |
| 6,017,340 A | 1/2000 | Cassidy et al. |
| 6,018,676 A | 1/2000 | Davis et al. |
| 6,030,380 A | 2/2000 | Auth et al. |
| 6,032,674 A | 3/2000 | Eggers et al. |
| 6,048,349 A | 4/2000 | Winston et al. |
| 6,053,870 A | 4/2000 | Fulton, III |
| 6,053,904 A | 4/2000 | Scribner et al. |
| 6,056,747 A | 5/2000 | Saadat et al. |
| 6,063,093 A | 5/2000 | Winston et al. |
| 6,093,185 A | 7/2000 | Ellis et al. |
| 6,106,515 A | 8/2000 | Winston et al. |
| 6,106,520 A | 8/2000 | Laufer et al. |
| 6,117,131 A | 9/2000 | Taylor |
| 6,142,992 A | 11/2000 | Cheng et al. |
| 6,146,380 A | 11/2000 | Racz et al. |
| 6,155,264 A | 12/2000 | Ressemann et al. |
| 6,156,031 A | 12/2000 | Aita et al. |
| 6,171,305 B1 | 1/2001 | Sherman |
| 6,179,824 B1 | 1/2001 | Eggers et al. |
| 6,193,676 B1 | 2/2001 | Winston et al. |
| 6,193,715 B1 | 2/2001 | Wrublewski et al. |
| 6,210,408 B1 | 4/2001 | Chandrasekaran et al. |
| 6,217,575 B1 | 4/2001 | Devore et al. |
| 6,221,061 B1 | 4/2001 | Engelson et al. |
| 6,228,076 B1 | 5/2001 | Winston et al. |
| 6,245,054 B1 | 6/2001 | Fuimaono et al. |
| 6,267,758 B1 | 7/2001 | Daw et al. |
| 6,283,983 B1 | 9/2001 | Makower et al. |
| 6,292,678 B1 | 9/2001 | Hall et al. |
| 6,293,945 B1 | 9/2001 | Parins et al. |
| 6,296,615 B1 | 10/2001 | Brockway et al. |
| 6,296,636 B1 | 10/2001 | Cheng et al. |
| 6,302,898 B1 | 10/2001 | Edwards et al. |
| 6,304,769 B1 | 10/2001 | Arenson et al. |
| 6,315,777 B1 | 11/2001 | Comben |
| 6,328,699 B1 | 12/2001 | Eigler et al. |
| 6,360,128 B2 | 3/2002 | Kordis et al. |
| 6,364,877 B1 | 4/2002 | Goble et al. |
| 6,385,472 B1 | 5/2002 | Hall et al. |
| 6,394,976 B1 | 5/2002 | Winston et al. |
| 6,395,002 B1 | 5/2002 | Ellman et al. |
| 6,419,674 B1 | 7/2002 | Bowser et al. |
| 6,423,051 B1 * | 7/2002 | Kaplan ............ A61M 25/0662 604/506 |
| 6,428,551 B1 | 8/2002 | Hall et al. |
| 6,450,989 B2 | 9/2002 | Dubrul et al. |
| 6,475,214 B1 | 11/2002 | Moaddeb |
| 6,485,485 B1 | 11/2002 | Winston et al. |
| 6,508,754 B1 | 1/2003 | Liprie et al. |
| 6,524,303 B1 | 2/2003 | Garibaldi |
| 6,530,923 B1 | 3/2003 | Dubrul et al. |
| 6,554,827 B2 | 4/2003 | Chandrasekaran et al. |
| 6,562,031 B2 | 5/2003 | Chandrasekaran et al. |
| 6,562,049 B1 | 5/2003 | Norlander et al. |
| 6,565,562 B1 | 5/2003 | Shah et al. |
| 6,607,529 B1 | 8/2003 | Jones et al. |
| 6,632,222 B1 | 10/2003 | Edwards et al. |
| 6,639,999 B1 | 10/2003 | Cookingham et al. |
| 6,650,923 B1 | 11/2003 | Lesh et al. |
| 6,651,672 B2 | 11/2003 | Roth |
| 6,662,034 B2 | 12/2003 | Segner et al. |
| 6,663,621 B1 | 12/2003 | Winston et al. |
| 6,702,811 B2 | 3/2004 | Stewart et al. |
| 6,709,444 B1 | 3/2004 | Makower |
| 6,723,052 B2 | 4/2004 | Mills |
| 6,733,511 B2 | 5/2004 | Hall et al. |

(56) References Cited

U.S. PATENT DOCUMENTS

| | | |
|---|---|---|
| 6,740,103 B2 | 5/2004 | Hall et al. |
| 6,752,800 B1 | 6/2004 | Winston et al. |
| 6,755,816 B2 | 6/2004 | Ritter et al. |
| 6,811,544 B2 | 11/2004 | Schaer |
| 6,814,733 B2 | 11/2004 | Schwartz et al. |
| 6,820,614 B2 | 11/2004 | Bonutti |
| 6,834,201 B2 | 12/2004 | Gillies et al. |
| 6,842,639 B1 | 1/2005 | Winston et al. |
| 6,852,109 B2 | 2/2005 | Winston et al. |
| 6,855,143 B2 | 2/2005 | Davison et al. |
| 6,860,856 B2 | 3/2005 | Ward et al. |
| 6,869,431 B2 | 3/2005 | Maguire et al. |
| 6,911,026 B1 | 6/2005 | Hall et al. |
| 6,951,554 B2 | 10/2005 | Johansen et al. |
| 6,951,555 B1 | 10/2005 | Suresh et al. |
| 6,955,675 B2 | 10/2005 | Jain |
| 6,970,732 B2 | 11/2005 | Winston et al. |
| 6,980,843 B2 | 12/2005 | Eng et al. |
| 7,029,470 B2 | 4/2006 | Francischelli et al. |
| 7,056,294 B2 | 6/2006 | Khairkhahan et al. |
| 7,083,566 B2 | 8/2006 | Tornes et al. |
| 7,112,197 B2 | 9/2006 | Hartley et al. |
| 7,335,197 B2 | 2/2008 | Sage et al. |
| 7,618,430 B2 | 11/2009 | Scheib |
| 7,651,492 B2 | 1/2010 | Wham |
| 7,666,203 B2 | 2/2010 | Chanduszko et al. |
| 7,678,081 B2 | 3/2010 | Whiting et al. |
| 7,682,360 B2 | 3/2010 | Guerra |
| 7,828,796 B2 | 11/2010 | Wong et al. |
| 7,900,928 B2 | 3/2011 | Held et al. |
| 8,192,425 B2 | 6/2012 | Mirza et al. |
| 8,257,323 B2 | 9/2012 | Joseph et al. |
| 8,388,549 B2 | 3/2013 | Paul et al. |
| 8,500,697 B2 | 8/2013 | Kurth et al. |
| 9,339,295 B2 * | 5/2016 | Fung ................ A61B 17/3478 |
| 11,339,579 B1 | 5/2022 | Stearns |
| 2001/0012934 A1 | 8/2001 | Chandrasekaran et al. |
| 2001/0021867 A1 | 9/2001 | Kordis et al. |
| 2002/0019644 A1 | 2/2002 | Hastings et al. |
| 2002/0022781 A1 | 2/2002 | McIntire et al. |
| 2002/0022836 A1 | 2/2002 | Goble et al. |
| 2002/0035361 A1 | 3/2002 | Houser et al. |
| 2002/0087153 A1 | 7/2002 | Roschak et al. |
| 2002/0087156 A1 | 7/2002 | Maguire et al. |
| 2002/0111618 A1 | 8/2002 | Stewart et al. |
| 2002/0123749 A1 | 9/2002 | Jain |
| 2002/0147485 A1 | 10/2002 | Mamo et al. |
| 2002/0169377 A1 | 11/2002 | Khairkhahan et al. |
| 2002/0188302 A1 | 12/2002 | Berg et al. |
| 2002/0198521 A1 | 12/2002 | Maguire |
| 2003/0032929 A1 | 2/2003 | Mcguckin |
| 2003/0040742 A1 | 2/2003 | Underwood et al. |
| 2003/0144658 A1 | 7/2003 | Schwartz et al. |
| 2003/0158480 A1 | 8/2003 | Tornes et al. |
| 2003/0163153 A1 | 8/2003 | Scheib |
| 2003/0225392 A1 | 12/2003 | Mcmichael et al. |
| 2004/0015162 A1 | 1/2004 | Mcgaffigan |
| 2004/0024396 A1 | 2/2004 | Eggers |
| 2004/0030328 A1 | 2/2004 | Eggers et al. |
| 2004/0044350 A1 | 3/2004 | Martin et al. |
| 2004/0073243 A1 | 4/2004 | Sepetka et al. |
| 2004/0077948 A1 | 4/2004 | Violante et al. |
| 2004/0116851 A1 | 6/2004 | Johansen et al. |
| 2004/0127963 A1 | 7/2004 | Uchida et al. |
| 2004/0133113 A1 | 7/2004 | Krishnan |
| 2004/0133130 A1 | 7/2004 | Ferry et al. |
| 2004/0143256 A1 | 7/2004 | Bednarek |
| 2004/0147950 A1 | 7/2004 | Mueller et al. |
| 2004/0181213 A1 | 9/2004 | Gondo |
| 2004/0230188 A1 | 11/2004 | Cioanta et al. |
| 2005/0004585 A1 | 1/2005 | Hall et al. |
| 2005/0010208 A1 | 1/2005 | Winston et al. |
| 2005/0049628 A1 | 3/2005 | Schweikert et al. |
| 2005/0059966 A1 | 3/2005 | Mcclurken et al. |
| 2005/0065507 A1 | 3/2005 | Hartley et al. |
| 2005/0085806 A1 | 4/2005 | Auge et al. |
| 2005/0096529 A1 | 5/2005 | Cooper et al. |
| 2005/0101984 A1 | 5/2005 | Chanduszko et al. |
| 2005/0119556 A1 | 6/2005 | Gillies et al. |
| 2005/0137527 A1 | 6/2005 | Kunin |
| 2005/0149012 A1 | 7/2005 | Penny et al. |
| 2005/0203504 A1 | 9/2005 | Wham et al. |
| 2005/0203507 A1 | 9/2005 | Truckai et al. |
| 2005/0261607 A1 | 11/2005 | Johansen et al. |
| 2005/0288631 A1 | 12/2005 | Lewis et al. |
| 2006/0041253 A1 | 2/2006 | Newton et al. |
| 2006/0074398 A1 | 4/2006 | Whiting et al. |
| 2006/0079769 A1 | 4/2006 | Whiting et al. |
| 2006/0079787 A1 | 4/2006 | Whiting et al. |
| 2006/0079884 A1 | 4/2006 | Manzo et al. |
| 2006/0085054 A1 | 4/2006 | Zikorus et al. |
| 2006/0089638 A1 | 4/2006 | Carmel et al. |
| 2006/0106375 A1 | 5/2006 | Werneth et al. |
| 2006/0135962 A1 | 6/2006 | Kick et al. |
| 2006/0142756 A1 | 6/2006 | Davies et al. |
| 2006/0189972 A1 | 8/2006 | Grossman |
| 2006/0241586 A1 | 10/2006 | Wilk |
| 2006/0247672 A1 | 11/2006 | Vidlund et al. |
| 2006/0264927 A1 | 11/2006 | Ryan |
| 2006/0276710 A1 | 12/2006 | Krishnan |
| 2007/0060879 A1 | 3/2007 | Weitzner et al. |
| 2007/0066975 A1 | 3/2007 | Wong et al. |
| 2007/0118099 A1 | 5/2007 | Trout, III |
| 2007/0123964 A1 | 5/2007 | Davies et al. |
| 2007/0167775 A1 | 7/2007 | Kochavi et al. |
| 2007/0208256 A1 | 9/2007 | Marilla |
| 2007/0225681 A1 | 9/2007 | House |
| 2007/0270791 A1 | 11/2007 | Wang et al. |
| 2008/0039865 A1 | 2/2008 | Shaher et al. |
| 2008/0042360 A1 | 2/2008 | Veikley |
| 2008/0086120 A1 | 4/2008 | Mirza et al. |
| 2008/0097213 A1 | 4/2008 | Carlson et al. |
| 2008/0108987 A1 | 5/2008 | Bruszewski et al. |
| 2008/0146918 A1 | 6/2008 | Magnin et al. |
| 2008/0171934 A1 | 7/2008 | Greenan et al. |
| 2008/0208121 A1 | 8/2008 | Youssef et al. |
| 2008/0275439 A1 | 11/2008 | Francischelli et al. |
| 2009/0105742 A1 | 4/2009 | Kurth et al. |
| 2009/0138009 A1 | 5/2009 | Viswanathan et al. |
| 2009/0163850 A1 | 6/2009 | Betts et al. |
| 2009/0177114 A1 | 7/2009 | Chin et al. |
| 2009/0264977 A1 | 10/2009 | Bruszewski et al. |
| 2010/0087789 A1 | 4/2010 | Leeflang et al. |
| 2010/0125282 A1 | 5/2010 | Machek et al. |
| 2010/0168684 A1 | 7/2010 | Ryan |
| 2010/0179632 A1 | 7/2010 | Bruszewski et al. |
| 2010/0191142 A1 | 7/2010 | Paul et al. |
| 2010/0194047 A1 | 8/2010 | Sauerwine |
| 2011/0046619 A1 | 2/2011 | Ducharme |
| 2011/0152716 A1 | 6/2011 | Chudzik et al. |
| 2011/0160592 A1 | 6/2011 | Mitchell |
| 2011/0190763 A1 | 8/2011 | Urban et al. |
| 2012/0232546 A1 | 9/2012 | Mirza et al. |
| 2012/0265055 A1 | 10/2012 | Melsheimer et al. |
| 2012/0330156 A1 | 12/2012 | Brown et al. |
| 2013/0184551 A1 | 7/2013 | Paganelli et al. |
| 2013/0184735 A1 | 7/2013 | Fischell et al. |
| 2013/0282084 A1 | 10/2013 | Mathur et al. |
| 2014/0206987 A1 | 7/2014 | Urbanski et al. |
| 2014/0296769 A1 | 10/2014 | Hyde et al. |
| 2016/0220741 A1 | 8/2016 | Garrison et al. |
| 2019/0021763 A1 | 1/2019 | Zhou et al. |
| 2019/0247035 A1 | 8/2019 | Gittard et al. |

* cited by examiner

CATHETER HAVING TISSUE-ENGAGING DEVICE

TECHNICAL FIELD

This document relates to the technical field of (and is not limited to) (A) a catheter having a tissue-engaging device (and method therefor), and/or (B) an elongated puncture device and a catheter having a tissue-engaging device (and method therefor).

BACKGROUND

Known medical devices are configured to facilitate a medical procedure, and help healthcare providers diagnose and/or treat medical conditions of sick patients.

SUMMARY

It will be appreciated that there exists a need to mitigate (at least in part) at least one problem associated with the existing (known) catheters used in procedures for formation of punctures. After much study of, and experimentation with, the existing (known) catheters, an understanding (at least in part) of the problem and its solution have been identified (at least in part) and are articulated (at least in part) as follows:

The pericardium (pericardium layer) is the outermost layer of the heart, surrounding the myocardium (the myocardium layer). The pericardium layer consists of two layers: an outer fibrous layer and an inner serous layer. The inner serous layer is further subdivided into two layers: an outer parietal layer and an inner visceral layer (also referred to as the epicardium layer), and immediately covers the myocardium layer (and the great vessels of the heart). Situated between the outer parietal layer of the epicardium layer is the pericardial cavity (pericardial space), a fluid-filled space typically containing approximately twenty milliliters (mL) of physiological fluid.

Certain cardiac conditions are treated by percutaneously inserting a needle through the pericardium layer into the pericardial cavity, and performing a procedure from within the pericardial cavity. For example, ventricular tachycardia is often treated by inserting a needle into the pericardial cavity to provide access to the epicardium layer for catheter mapping and ablation procedures. This technique uses a known epidural needle, which is inserted into the subxiphoid region, to puncture both the thoracic cavity and the outer layers of the pericardium layer. Once the needle has reached the pericardial cavity, catheter mapping and ablation procedures may be performed. For instance, a purpose for inserting the needle is to ultimately enable positioning of catheters in the pericardial space (if so desired). Additionally, the technique may use a known epidural needle and/or several other needle types may also work. Additionally, the property of the epidural needle or the tuohy-shaped needle, for this application, is that they are configured to be non-coring (that is, they do not form a tissue core).

This technique, however, has various risks associated with it, the most notable of which is the laceration of the myocardium layer by the needle. This risk may be heightened for the case where the pericardial cavity and/or the fluid volume (filling the pericardial cavity) is/are relatively small, leading to accidental right ventricular laceration.

There are known devices and/or methods for accessing the pericardial cavity, but these may be relatively invasive and carry further risks to the patient.

What may be desired is a device and/or method for providing access to the pericardial cavity while reducing risk of tissue damage (damage to the myocardial layer).

A challenge associated with gaining percutaneous access to the pericardial space is controlled puncture of the pericardium layer (of the heart) to access the pericardial space without damaging the underlying heart muscle. In healthy tissue, there is a lubricating film of pericardial fluid in this virtual space (the pericardial space), but in other instances due to disease and/or prior cardiac interventions, the pericardium layer and heart muscle may be fused (together) by scar tissue and/or adhesions.

It may be desirable to provide a controlled space (or landing zone) located between the pericardium layer and the heart muscle, which might improve the safety and/or predictability of tissue puncture using needles or other such medical tools.

To mitigate, at least in part, at least one problem associated with the existing technology, there is provided (in accordance with a major aspect) an apparatus. The apparatus is for use with a first biological wall positioned adjacent to (proximate to, located over) a second biological wall of a patient. The apparatus includes and is not limited to (comprises) an elongated catheter including a distal catheter section having a tissue-engaging device configured to be urged to move and contact a first surface (an outer surface) of the first biological wall. The tissue-engaging device extends, at least in part, from the distal catheter section. The tissue-engaging device is configured to be urged to puncture through the first biological wall after the tissue-engaging device has been urged to move and contact the first surface of the first biological wall. The tissue-engaging device is also configured to be urged to contact, at least in part, a first surface of the first biological wall without impinging the second biological wall after the tissue-engaging device has punctured through the first biological wall.

To mitigate, at least in part, at least one problem associated with the existing technology, there is provided (in accordance with a major aspect) an apparatus. The apparatus is for use with a first biological wall positioned adjacent to a second biological wall of a patient. The apparatus includes and is not limited to (comprises) an elongated puncture device. An elongated catheter includes a distal catheter section having a tissue-engaging device configured to be urged to move and contact a first surface of the first biological wall. The elongated catheter is configured to slidably guide, at least in part, movement of an elongated puncture device toward the tissue-engaging device. The elongated puncture device is configured to form a puncture passage extending through the first biological wall (that is, once or after the elongated puncture device is slidably guided, at least in part, toward the first biological wall and past the tissue-engaging device). The tissue-engaging device extends, at least in part, from the distal catheter section. The tissue-engaging device is configured to be urged to puncture through the first biological wall after the tissue-engaging device has been urged to move and contact the first surface of the first biological wall. The tissue-engaging device is also configured to be urged to contact, at least in part, a first surface of the first biological wall, without impinging the second biological wall, after the tissue-engaging device has punctured through the first biological wall. The tissue-engaging device is also configured to be selectively urged to contact, at least in part, a second surface of the first biological wall, without impinging the second biological wall, after the tissue-engaging device is urged to puncture (through) the first surface and then through the first biological wall; this is done, preferably, in such a way that the tissue-engaging device, in use, elastically stretches, at least in part, the first biological wall away from the second biological wall in response to the tissue-engaging device being urged to move away from the second biological wall, and the elongated puncture device is movable to puncture (through) the first biological wall.

To mitigate, at least in part, at least one problem associated with the existing technology, there is provided (in accordance with a major aspect) a method. The method is for using (positioning) an elongated puncture device configured to form a puncture passage extending through a first biological wall. The first biological wall is positioned adjacent to (located over) a second biological wall of a patient. The method includes and is not limited to (comprises) maneuvering an elongated catheter having a distal catheter section toward the first biological wall, and the distal catheter section is rotatable, at least in part, about a longitudinal axis extending along the elongated catheter, and a tissue-engaging device is securely mounted to, and extends from, the distal catheter section. The method also includes selectively engaging, at least in part, the tissue-engaging device with the first biological wall without engaging the second biological wall. The method also includes moving the tissue-engaging device away from the second biological wall thereby elastically stretching the first biological wall away from the second biological wall while the tissue-engaging device remains selectively engaged with the first biological wall. The method also includes slidably receiving, at least in part, the elongated puncture device, along the elongated catheter. The method also includes guiding, at least in part, movement of the elongated puncture device toward the first biological wall (the first biological wall is engaged with the tissue-engaging device that extends from the distal catheter section). The method also includes using the elongated puncture device to puncture the first biological wall (that is engaged with the tissue-engaging device).

Other aspects are identified in the claims. Other aspects and features of the non-limiting embodiments may now become apparent to those skilled in the art upon review of the following detailed description of the non-limiting embodiments with the accompanying drawings. This Summary is provided to introduce concepts in simplified form that are further described below in the Detailed Description. This Summary is not intended to identify potentially key features or possible essential features of the disclosed subject matter, and is not intended to describe each disclosed embodiment or every implementation of the disclosed subject matter. Many other novel advantages, features, and relationships will become apparent as this description proceeds. The figures and the description that follow more particularly exemplify illustrative embodiments.

BRIEF DESCRIPTION OF THE DRAWINGS

The non-limiting embodiments may be more fully appreciated by reference to the following detailed description of the non-limiting embodiments when taken in conjunction with the accompanying drawings, in which.

Figure 1:
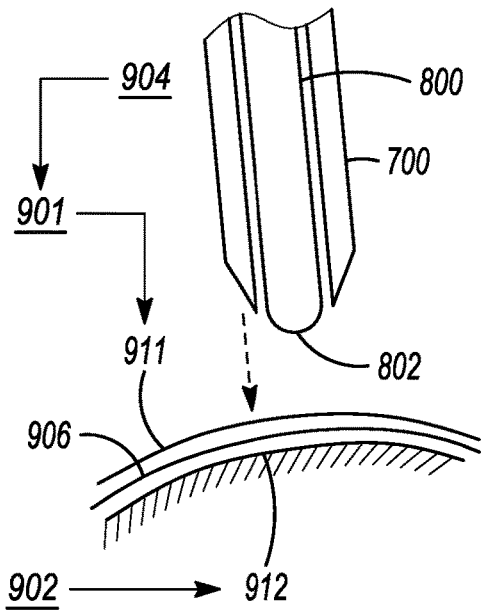
FIG. 1 and FIG. 2 depict side cross-sectional views of embodiments of an introducer assembly.

The drawings are not necessarily to scale and may be illustrated by phantom lines, diagrammatic representations and fragmentary views. In certain instances, details unnecessary for an understanding of the embodiments (and/or details that render other details difficult to perceive) may have been omitted. Corresponding reference characters indicate corresponding components throughout the several figures of the drawings. Elements in the several figures are illustrated for simplicity and clarity and have not been drawn to scale. The dimensions of some of the elements in the figures may be emphasized relative to other elements for facilitating an understanding of the various disclosed embodiments. In addition, common, and well-understood, elements that are useful in commercially feasible embodiments are often not depicted to provide a less obstructed view of the embodiments of the present disclosure.

LISTING OF REFERENCE NUMERALS USED IN THE DRAWINGS

| | |
|---|---|
| catheter 102 | introducer assembly 700 |
| longitudinal axis 103 | puncture device 800 |
| distal catheter section 104 | distal puncture portion 802 |
| catheter lumen 105 | puncture passage 900 |
| tissue-engaging device 106 | first biological wall 901 |
| curved tines (108A, 108B) | second biological wall 902 |
| curved tine grooves (110A, 110B) | patient 904 |
| tine tips (111A, 111B) | biological space 906 |
| inner diameter 112 | pericardium layer 911 |
| outer diameter 114 | myocardium layer 912 |
| spiral formation 116 | first surface 921 |
| spiral tip 118 | second surface 922 |
| spiral spacing 120 | |

DETAILED DESCRIPTION OF THE NON-LIMITING EMBODIMENT(S)

The following detailed description is merely exemplary and is not intended to limit the described embodiments or the application and uses of the described embodiments. As used, the word "exemplary" or "illustrative" means "serving as an example, instance, or illustration." Any implementation described as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure. The scope of the disclosure is defined by the claims. For the description, the terms "upper," "lower," "left," "rear," "right," "front," "vertical," "horizontal," and derivatives thereof shall relate to the examples as oriented in the drawings. There is no intention to be bound by any expressed or implied theory in the preceding Technical Field, Background, Summary or the following detailed description. It is also to be understood that the devices and processes illustrated in the attached drawings, and described in the following specification, are exemplary embodiments (examples), aspects and/or concepts defined in the appended claims. Hence, dimensions and other physical characteristics relating to the embodiments disclosed are not to be considered as limiting, unless the claims expressly state otherwise. It is understood that the phrase "at least one" is equivalent to "a". The aspects (examples, alterations, modifications, options, variations, embodiments and any equivalent thereof) are described regarding the drawings. It should be understood that the disclosure is limited to the subject matter provided by the claims, and that the disclosure is not limited to the particular aspects depicted and described. It will be appreciated that the scope of the meaning of a device configured to be coupled to an item (that is, to be connected to, to interact with the item, etc.) is to be interpreted as the device being configured to be coupled to the item, either directly or indirectly. Therefore, "configured to" may include the meaning "either directly or indirectly" unless specifically stated otherwise.

Figure 2:
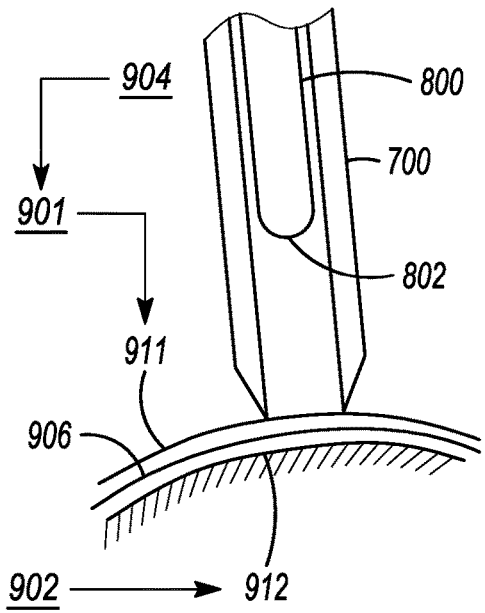

FIG. 1 and FIG. 2 depict side cross-sectional views of embodiments of an introducer assembly 700.

Referring to the embodiment as depicted in FIG. 1, the distal section of the introducer assembly 700 is maneuvered proximate to the first biological wall 901 (or the pericardium layer 911) of the patient 904. The first biological wall 901 is positioned proximate to (over) the second biological wall 902 (or the myocardium layer 912). The pericardium layer 911 is the outermost layer of the heart of the patient 904. The pericardium layer 911 surrounds the myocardium layer 912 of the heart. A biological space 906 may be defined or formed between the first biological wall 901 (or the pericardium layer 911) and the second biological wall 902 (or the myocardium layer 912). The introducer assembly 700 is configured to receive and to guide the movement of the puncture device 800, having a distal puncture portion 802, toward the first biological wall 901 (or the pericardium layer 911).

The distal puncture portion 802 is configured to form a puncture passageway through the first biological wall 901 (or the pericardium layer 911) after the distal puncture portion 802 is positioned proximate to the first biological wall 901 (or the pericardium layer 911).

It may be desired to not inflict any damage to the second biological wall 902 (or the myocardium layer 912) while or after the distal puncture portion 802 forms the puncture passageway through the first biological wall 901 (or the pericardium layer 911).

Referring to the embodiment as depicted in FIG. 2, the distal section of the introducer assembly 700 is maneuvered to contact the outer surface of the first biological wall 901 (or the pericardium layer 911). The distal puncture portion 802 is movable toward the first biological wall 901 (or the pericardium layer 911) after the distal section of the introducer assembly 700 makes contact with the outer surface of the first biological wall 901 (or the pericardium layer 911). The introducer assembly 700 makes contact with the outer surface of the first biological wall 901 (or the pericardium layer 911) in order to stabilize the position of the distal puncture portion 802 relative to the first biological wall 901 before utilizing the distal puncture portion 802.

Figure 3:
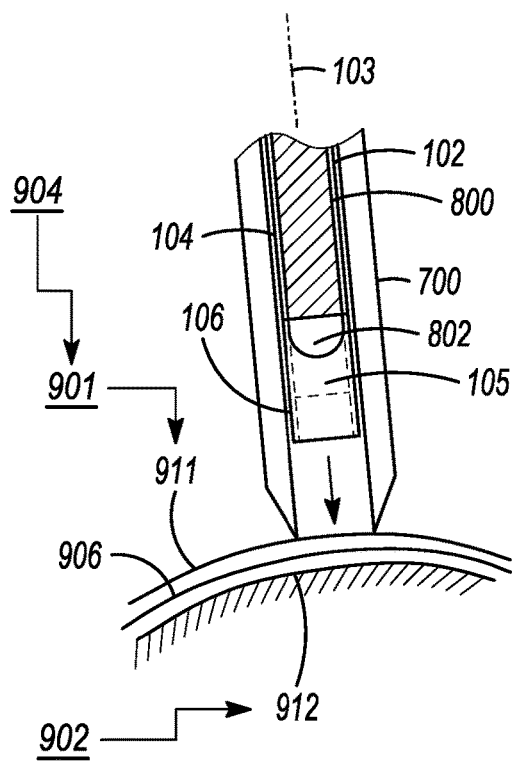
FIG. 3 depicts a side cross-sectional view of an embodiment of an elongated catheter having a tissue-engaging device for use with the introducer assembly of FIG. 1.

FIG. 3 depicts a side cross-sectional view of embodiments of an elongated catheter 102 having a tissue-engaging device 106 for use with the introducer assembly 700 of FIG. 1.

Figure 5:
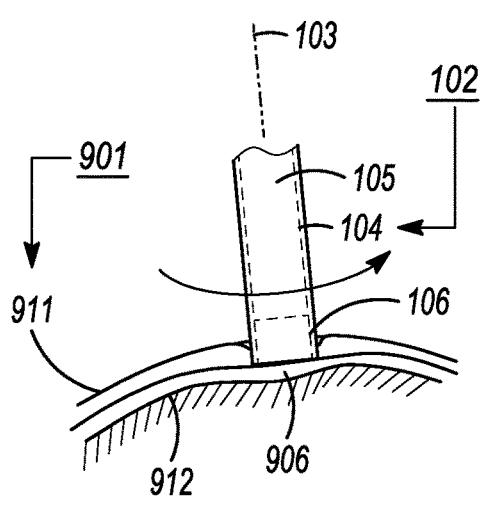

Referring to the embodiment as depicted in FIG. 3, the introducer assembly 700 is positioned to contact (the outer surface of) the first biological wall 901 (or the pericardium layer 911). The introducer assembly 700 is configured to receive, and guide the movement of, the elongated catheter 102. The elongated catheter 102 is configured to be introduced into, and extend along, the interior of the introducer assembly 700. The longitudinal axis 103 extends along a length of the elongated catheter 102. The distal catheter section 104 extends distally from the elongated catheter 102. The elongated catheter 102 defines the catheter lumen 105 configured to receive the puncture device 800 having the distal puncture portion 802. The tissue-engaging device 106 extends (distally) from the distal catheter section 104. The tissue-engaging device 106 is moved toward the first biological wall 901 (or the pericardium layer 911), and contacts the first biological wall 901. The puncture device 800, having the distal puncture portion 802, is movable along the catheter lumen 105 (defined by the elongated catheter 102). The tissue-engaging device 106 is movable toward, and is contactable with, the first biological wall 901 (or the pericardium layer 911). The tissue-engaging device 106 is configured to selectively engage with (auger into) the first biological wall 901 (or the pericardium layer 911) without damaging the second biological wall 902 (or the myocardium layer 912). After the tissue-engaging device 106, in use, is maneuvered to contact the first biological wall 901, the elongated catheter 102 is rotated and thereby rotates the tissue-engaging device 106 (to urge rotational motion to the tissue-engaging device 106) as seen in FIGS. 5 and 11. The tissue-engaging device 106 may be integrated with, or may be separately attachable from, the distal catheter section 104. The tissue-engaging device 106 may include, for instance, tines (as depicted in FIG. 10 to FIG. 15) or a spiral formation (as depicted in FIG. 16 to FIG. 19) configured to selectively capture or engage biological tissue. The tissue-engaging device 106 may be configured to provide a bite depth; the bite depth may depend on the size of anatomical features of the biological tissues (to mitigate trauma to underlying tissues or biological features or layers). It will be appreciated that integrated flushing ports, round corners, and/or a tapered profile may improve an ability to confirm positioning, and/or selection, of tissue, etc. The introducer assembly 700 and/or the elongated catheter 102 are configured to be inserted into a confined space defined by a living body (the patient).

Referring to the embodiment as depicted in FIG. 3, the components of the elongated catheter 102 include biocompatible material properties suitable for sufficient performance (such as dielectric strength, thermal performance, insulation and corrosion, water resistance and/or heat resistance) for compliance with industrial and regulatory safety standards (or compatible for medical usage), etc. Reference is made to the following publication for consideration in the selection of a suitable material: Plastics in Medical Devices: Properties, Requirements, and Applications; 2nd Edition; author: Vinny R. Sastri; hardcover ISBN: 9781455732012; published: 21 Nov. 2013; publisher: Amsterdam [Pays-Bas]: Elsevier/William Andrew, [2014]. The components of the elongated catheter 102 may include a shape-memory material configured to be manipulated and/or deformed followed by a return to the original shape that the shape-memory material was set in (prior to manipulation). Shape-memory materials (SMMs) are known and not further described in detail. Shape-memory materials are configured to recover their original shape from a significant and seemingly plastic deformation in response to a particular stimulus applied to the shape-memory material. This is known as the shape memory effect (SME). Superelasticity (in alloys) may be observed once the shape-memory material is deformed under the presence (an application) of a stimulus force. It will be appreciated that the description regarding shape memory alloys is not critical, though such materials may be utilized. However, preferable materials may include medical-grade stainless steel alloys that are commonly used for needles and/or cannulas; these may provide reasonable materials for this application owing to their strength and/or other characteristics (such as, torquability, pushability, etc.), availability in thin wall hypotube profiles, and/or processability (using Electrical Discharge Machining (EDM), laser cutting, etc.) to form the distal retraction mechanism, etc.

FIG. 4 to FIG. 9 depict side cross-sectional views of embodiments of the elongated catheter 102 and the tissue-engaging device 106 of FIG. 3 (for depicting the workflow for capturing and puncturing the first biological wall 901). It will be appreciated that the introducer assembly 700 (as depicted in FIG. 1) is not depicted in FIG. 4 to FIG. 19 in order to improve the views of the elongated catheter 102 and the tissue-engaging device 106.

Figure 4:
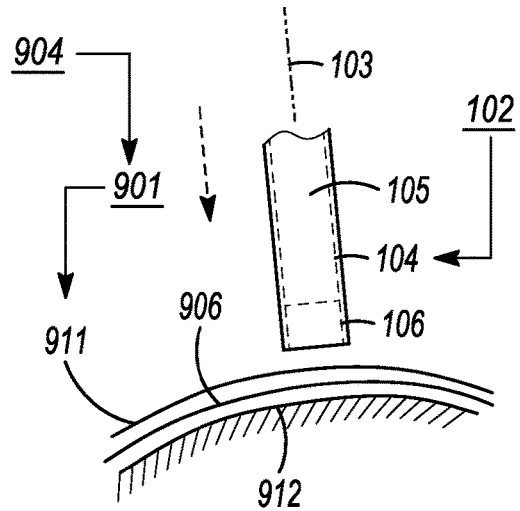
FIG. 4 to FIG. 9 depict side cross-sectional views of embodiments of the elongated catheter and the tissue-engaging device of FIG. 3.

Referring to the embodiment as depicted in FIG. 4, the tissue-engaging device 106 extends from the distal catheter section 104 of the elongated catheter 102. The longitudinal axis 103 extends along the tissue-engaging device 106 of the elongated catheter 102. The tissue-engaging device 106, the distal catheter section 104 and the elongated catheter 102 define the catheter lumen 105. The tissue-engaging device 106 of the elongated catheter 102 is urged to move toward (and proximal to) the first biological wall 901 (or the pericardium layer 911) of the patient 904. The tissue-engaging device 106, in use, is further urged to make contact with the first biological wall 901 (or the pericardium layer 911). The second biological wall 902 (or the myocardium layer 912) is positioned proximate to the first biological wall 901. The biological space 906 (also known as the pericardial cavity) is positioned (located) between the second biological wall 902 and the first biological wall 901. In accordance with an embodiment, the first biological wall 901 includes the pericardium layer 911, and the second biological wall 902 includes the myocardium layer 912. The pericardium layer 911 is the outermost layer of the heart of the patient 904. The pericardium layer 911 surrounds the myocardium layer 912 of the heart.

Referring to the embodiment as depicted in FIG. 5, the tissue-engaging device 106 has moved toward, and made contact with, the first biological wall 901 (or the pericardium layer 911). The tissue-engaging device 106 is rotated (twisted) along the longitudinal axis 103 after the tissue-engaging device 106 has contacted the first biological wall 901 (or the pericardium layer 911) without, preferably, contacting and/or damaging the second biological wall 902. The tissue-engaging device 106 enters (at least in part) the biological space 906 formed between the first biological wall 901 and the second biological wall 902. The tissue-engaging device 106 selectively engages the first biological wall 901 (or the pericardium layer 911), without damaging the second biological wall 902; this is done, preferably, in response to rotation (twisting or movement) of the tissue-engaging device 106 along the longitudinal axis 103 while the tissue-engaging device 106 remains in contact (at least in part) with the first biological wall 901 (or the pericardium layer 911) and after the tissue-engaging device 106 enters (at least in part) into the biological space 906.

Referring to the embodiment as depicted in FIG. 5, the tissue-engaging device 106 is rotatable, at least in part, about a longitudinal axis 103 extending, at least in part, along the elongated catheter 102 in response to rotation of the elongated catheter 102. The tissue-engaging device 106 is also configured to be selectively urged to rotatably contact, at least in part, the second surface 922 of the first biological wall 901, without impinging the second biological wall 902.

Referring to the embodiment as depicted in FIG. 5, the tissue-engaging device 106 is also configured to be movable into a biological space 906 located between the first biological wall 901 and the second biological wall 902; this is done, preferably, in such a way that the tissue-engaging device 106 is spaced apart from the second biological wall 902 without engaging the second biological wall 902.

Referring to the embodiments as depicted in FIG. 5, the tissue-engaging device 106 is configured to selectively engage, at least in part, the first biological wall 901 in response to rotation of the distal catheter section 104 for urging the tissue-engaging device 106 to selectively engage with (auger into) a second surface 922 of the first biological wall 901 after the tissue-engaging device 106 has been maneuvered to contact the first biological wall 901.

Figure 6:
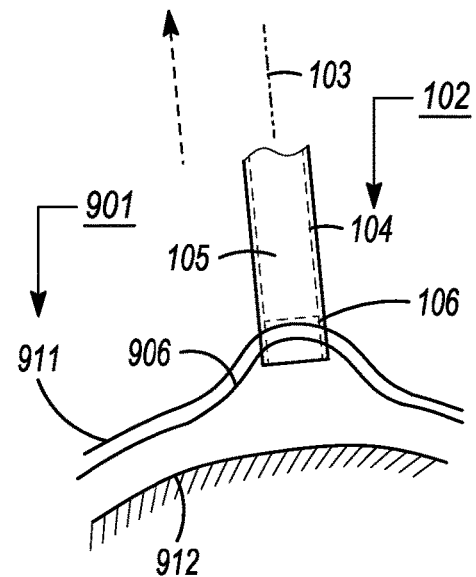

Referring to the embodiment as depicted in FIG. 6, the tissue-engaging device 106 has selectively engaged the first biological wall 901 (or the pericardium layer 911). The tissue-engaging device 106 is moved away (retracted along the longitudinal axis 103 and away) from the second biological wall 902 (or the myocardium layer 912); this is done, preferably, in such a way that the first biological wall 901 (or the pericardium layer 911) becomes stretched away from the second biological wall 902 (or the myocardium layer 912); in this manner, the biological space 906 becomes widened (in comparison to the widening of the biological space 906 as depicted in FIG. 5) that is positioned between the first biological wall 901 and the second biological wall 902.

Referring to the embodiments as depicted in FIG. 6, the tissue-engaging device 106 is also configured to remain engaged with the first biological wall 901 while the distal catheter section 104 is moved away from the second biological wall 902; in this manner, the tissue-engaging device 106 elastically stretches the first biological wall 901 away from the second biological wall 902, and locally enlarges the biological space 906 that is located proximate to the tissue-engaging device 106.

Referring to the embodiments as depicted in FIG. 5 and FIG. 6, the elongated catheter 102 is for use with the first biological wall 901 positioned adjacent to (proximate to, located over) the second biological wall 902 of the patient 904. The elongated catheter 102 includes the distal catheter section 104 having the tissue-engaging device 106 configured to be urged to move and contact a first surface 921 (such as an outer surface, as depicted in FIG. 11 and/or in FIG. 17) of the first biological wall 901 (as depicted in FIG. 5). The tissue-engaging device 106 extends, at least in part, from the distal catheter section 104 (as depicted in FIG. 5). The tissue-engaging device 106 is configured to be urged to puncture through the first biological wall 901 after the tissue-engaging device 106 has been urged to move and contact the first surface 921 of the first biological wall 901 (as depicted in FIG. 5). The tissue-engaging device 106 is also configured to be urged to contact, at least in part, the first surface 921 (as depicted in FIG. 11 and/or in FIG. 17) of the first biological wall 901, without impinging the second biological wall 902 (as depicted in FIG. 6); this is done, preferably, after the tissue-engaging device 106 has punctured through the first biological wall 901 (as depicted in FIG. 5 and FIG. 6).

Referring to the embodiment as depicted in FIG. 6, the elongated catheter 102 is configured to slidably guide, at least in part, movement of an elongated puncture device 800 toward the tissue-engaging device 106, and the elongated puncture device 800 is configured to form a puncture passage 900 extending through the first biological wall 901 after the elongated puncture device 800 is slidably guided, at least in part, toward the first biological wall 901 and past the tissue-engaging device 106. The tissue-engaging device 106 is also configured to be selectively urged to contact, at least in part, a portion of a second surface 922 (as depicted in FIG. 13 to FIG. 15 or FIG. 18 and FIG. 19 or FIGS. 11 and 17 in sideview) of the first biological wall 901; this is done, preferably, without impinging the second biological wall 902 after the tissue-engaging device 106 is urged to puncture through the first biological wall 901; this is done, preferably, in such a way that the tissue-engaging device 106, in use, elastically stretches a section of the first biological wall 901 away from the second biological wall 902 (in response to the tissue-engaging device 106 urged to move away from the second biological wall 902 while the elongated puncture device 800 is moved to puncture through the portion of the first biological wall 901 that is engaged by the tissue-engaging device 106). The elongated puncture device 800 may include (and is not limited to) a radio frequency puncture device, such as the BAYLIS (TRADEMARK) POWERWIRE (REGISTERED TRADEMARK) radio frequency guidewire manufactured by BAYLIS MEDICAL COMPANY (headquartered in Canada). In accordance with another embodiment, the elongated puncture device 800 includes (and is not limited to) an elongated guidewire having a distal tip section presenting a mechanical cutting portion. It will be appreciated that the elongated puncture device 800 may include any type of puncturing device. Preferably, the elongated puncture device 800 includes a blunt distal portion configured to selectively puncture by emission of radiofrequency (as opposed to the mechanical puncture device).

Figure 7:
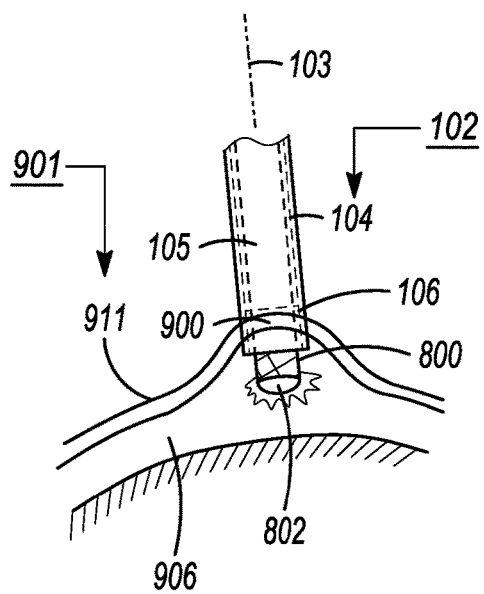

Referring to the embodiment as depicted in FIG. 7, the puncture device 800 is maneuvered along the elongated catheter 102 and the tissue-engaging device 106 toward the first biological wall 901. This is done, preferably, in such a way that the distal puncture portion 802 of the puncture device 800 is positioned proximate to, and faces, the first biological wall 901. The distal puncture portion 802 is configured for the formation of the puncture passage 900 to be extended through the first biological wall 901 (or the pericardium layer 911) without damaging the second biological wall 902 (or the myocardium layer 912). The distal puncture portion 802 may enter the biological space 906 without damaging the second biological wall 902 (or the myocardium layer 912).

Referring to the embodiments as depicted in FIG. 6 and FIG. 7, the elongated catheter 102 is configured to slidably guide, at least in part, movement of an elongated puncture device 800 toward the tissue-engaging device 106. The elongated puncture device 800 is configured to form a puncture passage 900 extending through the first biological wall 901 after the elongated puncture device 800 is slidably guided, at least in part, toward the first biological wall 901 and past the tissue-engaging device 106. The tissue-engaging device 106 is configured to maintain separation between the first biological wall 901 and the second biological wall 902 while the elongated puncture device 800 is maneuvered, along the elongated catheter 102, and positioned to form the puncture passage 900 extending through the first biological wall 901 without inadvertently damaging the second biological wall 902.

Referring to the embodiments as depicted in FIG. 7, the elongated catheter 102 is configured to slidably guide, at least in part, movement of an elongated puncture device 800 toward the tissue-engaging device 106. The elongated puncture device 800 is configured to form a puncture passage 900 extending through the first biological wall 901 after the elongated puncture device 800 is slidably guided, at least in part, toward the first biological wall 901 and past the tissue-engaging device 106. The tissue-engaging device 106 is also configured to maintain engagement with the first biological wall 901 while the elongated puncture device 800, in use, is maneuvered along the elongated catheter 102 toward the first biological wall 901 (via the distal catheter section 104). The elongated puncture device 800 is configured to form the puncture passage 900 extending through the first biological wall 901 without imparting damage to the second biological wall 902.

Referring to the embodiments as depicted in FIG. 7, the elongated catheter 102 is configured to slidably guide, at least in part, movement of an elongated puncture device 800 toward the tissue-engaging device 106. The elongated puncture device 800 is configured to form a puncture passage 900 extending through the first biological wall 901 after the elongated puncture device 800 is slidably guided, at least in part, toward the first biological wall 901 and past the tissue-engaging device 106. The elongated catheter 102 defines the elongated catheter lumen 105 extending, at least in part, along the distal catheter section 104. The elongated catheter lumen 105 is configured to slidably receive and guide the movement of the elongated puncture device 800 for exterior extension of the elongated puncture device 800 from the distal catheter section 104.

Referring to the embodiments as depicted in FIG. 7, the elongated catheter 102 includes the distal catheter section 104 having the tissue-engaging device 106 configured to be urged to move and contact a first surface 921 of the first biological wall 901. The elongated catheter 102 is configured to slidably guide, at least in part, movement of an elongated puncture device 800 toward the tissue-engaging device 106. The elongated puncture device 800 is configured to form the puncture passage 900 extending through the first biological wall 901 after the elongated puncture device 800 is slidably guided, at least in part, toward the first biological wall 901 and past the tissue-engaging device 106. The tissue-engaging device 106 extends, at least in part, from the distal catheter section 104. The tissue-engaging device 106 is configured to be urged to puncture through the first biological wall 901 after the tissue-engaging device 106 has been urged to move and contact the first surface 921 of the first biological wall 901. The tissue-engaging device 106 is also configured to be urged to contact, at least in part, a first surface 921 of the first biological wall 901 without impinging the second biological wall 902 (after the tissue-engaging device 106 has punctured through the first biological wall 901). The tissue-engaging device 106 is also configured to be selectively urged to contact, at least in part, a second surface 922 of the first biological wall 901 (preferably without impinging the second biological wall 902); this is done, preferably, after the tissue-engaging device 106 is urged to puncture past the first surface 921 and through the first biological wall 901; this is done, preferably, in such a way that the tissue-engaging device 106, in use, elastically stretches, at least in part, the first biological wall 901 away from the second biological wall 902 in response to the tissue-engaging device 106 being urged to move away from the second biological wall 902 (the elongated puncture device 800 is movable to puncture through the first biological wall 901). It will be appreciated that the elongated puncture device may also include a combination of a smaller needle and a guidewire (such as what is used for epicardial access with the micropuncture technique); that is, the needle performs the puncturing (formation of puncture), and then a wire (guidewire) is advanced.

Figure 8:
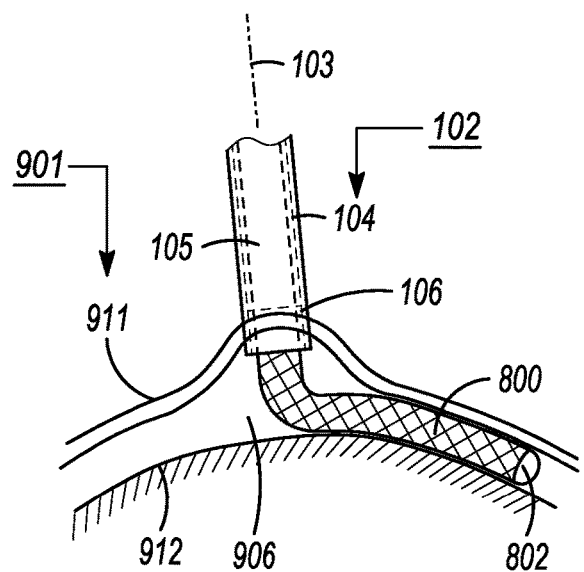

Referring to the embodiment as depicted in FIG. 8, a distal length of the puncture device 800 is maneuvered to extend from the elongated catheter 102 and the tissue-engaging device 106 and into the biological space 906 (that is, after the puncture portion 802 has formed the puncture passage 900 extending through the first biological wall 901 or the pericardium layer 911).

Figure 9:
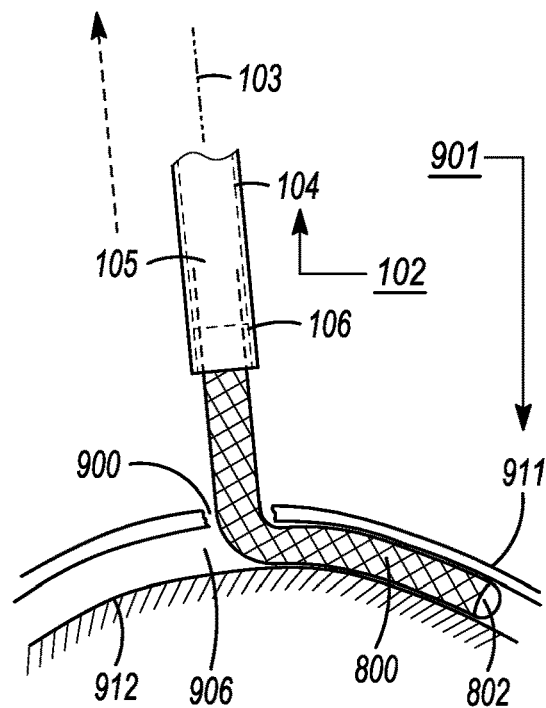

Referring to the embodiment as depicted in FIG. 9, the tissue-engaging device 106 is rotated so that the tissue-engaging device 106 becomes disengaged from the first biological wall 901 (or the pericardium layer 911). The distal section of the puncture device 800 remains in position in the biological space 906 between the first biological wall 901 (or the pericardium layer 911) and the second biological wall 902 (of the myocardium layer 912).

Referring to the embodiment as depicted in FIG. 9, the tissue-engaging device 106 is also configured to selectively disengage from the first biological wall 901 in response to rotation of the distal catheter section 104 about a longitudinal axis 103 extending along the elongated catheter 102.

Referring to the embodiments as depicted in FIG. 4 to FIG. 7, there is a method provided for using the elongated puncture device 800. The elongated puncture device 800 is configured to form the puncture passage 900 extending through the first biological wall 901. The method includes maneuvering the elongated catheter 102 having the distal catheter section 104 toward the first biological wall 901 (the distal catheter section 104 is rotatable, at least in part, about a longitudinal axis 103 extending along the elongated catheter 102) (as depicted in FIG. 4). The tissue-engaging device 106 is securely mounted to, and extends from, the distal catheter section 104 (as depicted in FIG. 4). The method also includes selectively engaging, at least in part, the tissue-engaging device 106 with the first biological wall 901 without engaging the second biological wall 902 (as depicted in FIG. 5). The method also includes moving the tissue-engaging device 106 away from the second biological wall 902 thereby elastically stretching the first biological wall 901 away from the second biological wall 902 while the tissue-engaging device 106 remains selectively engaged with the first biological wall 901 (as depicted in FIG. 6). The method also includes slidably receiving, at least in part, the elongated puncture device 800, along the elongated catheter 102 (as depicted in FIG. 7). It will be appreciated that the elongated puncture device may also include a combination of a smaller needle and a guidewire (such as what is used for epicardial access with the micropuncture technique); that is, the needle performs the puncturing (formation of puncture), and then a wire (guidewire) is advanced.

The method also includes guiding, at least in part, movement of the elongated puncture device 800 toward the first biological wall 901 that is engaged with the tissue-engaging device 106 extending from the distal catheter section 104 (as depicted in FIG. 7). The method also includes using the elongated puncture device 800 to puncture the first biological wall 901 that is engaged with the tissue-engaging device 106 (as depicted in FIG. 7).

FIG. 10 to FIG. 15 depict a perspective view (FIG. 10), side views (FIG. 11 and FIG. 12) and bottom views (FIG. 13 to FIG. 15) of embodiments of the tissue-engaging device 106 of FIG. 3.

Figure 10:
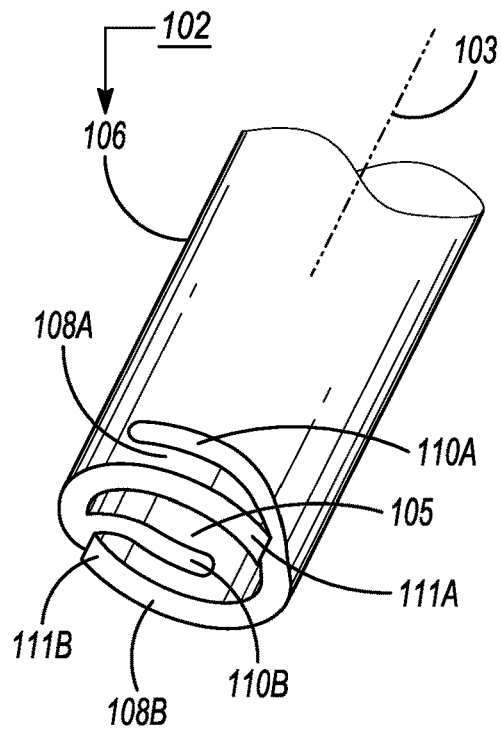
FIG. 10 to FIG. 15 depict a perspective view (FIG. 10), side views (FIG. 11 and FIG. 12) and bottom views (FIG. 13 to FIG. 15) of embodiments of the tissue-engaging device of FIG. 3.
Figure 11:
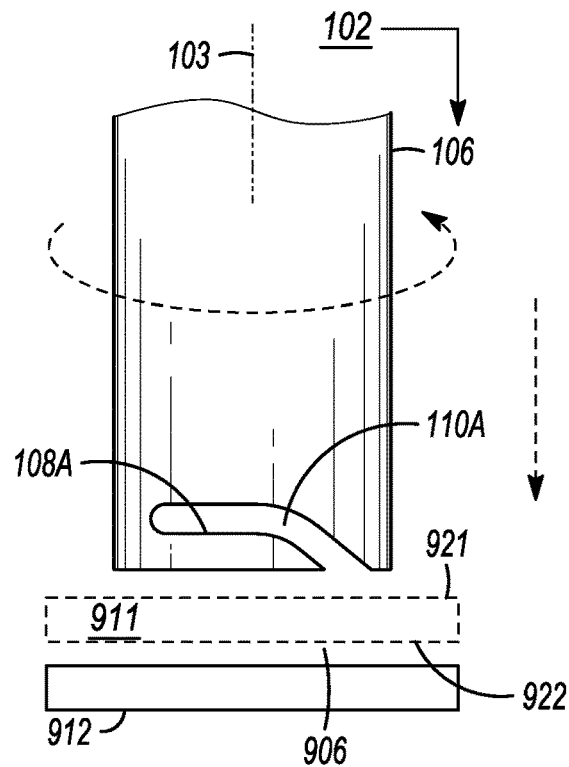

Referring to the embodiment as depicted in FIG. 10 (showing a perspective side view), the tissue-engaging device 106 includes curved tines (108A, 108B). The curved tines (108A, 108B) are positioned on opposite sides of the tissue-engaging device 106. The curved tines (108A, 108B) are positioned on, and extend from, the circumferential edge of the tissue-engaging device 106. The curved tines (108A, 108B) are spaced apart from each other. The catheter lumen 105 is positioned between the curved tines (108A, 108B). Positioned between the distal portion of the tissue-engaging device 106 and the curved tines (108A, 108B) are respective curved tine grooves (110A, 110B). The curved tines (108A, 108B) each includes, respectively, tine tips (111A, 111B) configured to bite into, and puncture through, the first biological wall 901 (or the pericardium layer 911) in response to rotational movement of the tissue-engaging device 106. The curved tine grooves (110A, 110B) are configured to receive (at least in part) a portion of the first biological wall 901 (or the pericardium layer 911) once (after) the first biological wall 901 (or the pericardium layer 911) is punctured by the tine tips (111A, 111B). The tine tips (111A, 111B) extend from respective portions of the curved tines (108A, 108B). In this manner, at least one of the tine tips (111A, 111B) may be in good (secure) contact with the first biological wall 901 (or the pericardium layer 911), depending on the angle of approach between the tissue-engaging device 106 and the first biological wall 901.

Referring to the embodiment as depicted in FIG. 11 (showing a side view), the tine tip 111A (also called the puncturing portion) of the curved tine 108A is positioned proximate to (for contacting) the first surface 921 (outer surface) of the first biological wall 901 (or the pericardium layer 911). Puncturing of the first biological wall 901 (or the pericardium layer 911) by the tine tip 111A is to be performed in response to movement (curved or rotational movement, around the longitudinal axis 103) of the tissue-engaging device 106 along with translation (linear movement) of the tissue-engaging device 106 further toward the first biological wall 901 (or the pericardium layer 911); in this manner, the curved tine 108A may auger (rotationally urge) the tine tip 111A through the first biological wall 901 (or the pericardium layer 911) from the first surface 921 (outer surface) to the second surface 922 (inner surface). Rotational movement of the tissue-engaging device 106 is configured to urge rotational (twisted) movement of the curved tine 108A and the tine tip 111A into the first biological wall 901 (or the pericardium layer 911). The inner diameter 112 is configured to slidably receive, and guide the movement of, the elongated puncture device 800 (as depicted in FIG. 7) toward the first surface 921 of the first biological wall 901 (or the pericardium layer 911).

Referring to the embodiment as depicted in FIG. 11, the curved tines (108A, 108B) are positioned in such a way that the tissue-engaging device 106 may be rotated by less than 180 degrees; in this manner, the curved tines (108A, 108B), advantageously, may facilitate less time for rotating (twisting) to engage (bite into) the curved tines (108A, 108B) with the first biological wall 901 (or the pericardium layer 911). Moreover, the curved tines (108A, 108B), advantageously, may provide at least two or more puncture points (that is the tine tips (111A, 111B), respectively) for biting into the first biological wall 901. For instance, if one of the curved tines fails to bit into (and engage with) the first biological wall 901, the other curved tine may be positioned to bite and engage with the first biological wall 901 (as a back-up for the curved tine that failed to bite and engage); it will be appreciated that depending on the angle of approach between the tissue-engaging device 106 and the first biological wall 901, one of the curved tines might not be in a good position to bite and engage with the and the first biological wall 901. Moreover, the curved tines (108A, 108B), advantageously, may provide improved engagement with the first biological wall 901 (the top surface of the curved tine 108A is flat and may be parallel to the first biological wall 901 when pulling back the first biological wall 901 (as depicted in FIG. 7). Moreover, the curved tines (108A, 108B), advantageously, may provide a top surface that is flat and parallel to the first biological wall 901 thereby providing for increased friction between the curved tines (108A, 108B) and the first biological wall 901 and reducing the possibility of unwanted slipping between the tissue-engaging device 106 and the first biological wall 901. Alternatively, it will be appreciated that the curved tines (108A, 108B) may, advantageously, provide at least two or more curved tines (108A, 108B), such as three curved tines (in which case the tissue-engaging device 106 may be rotated less than 120 degrees for urging the three curved tines to bite and engage the first biological wall 901).

Figure 12:
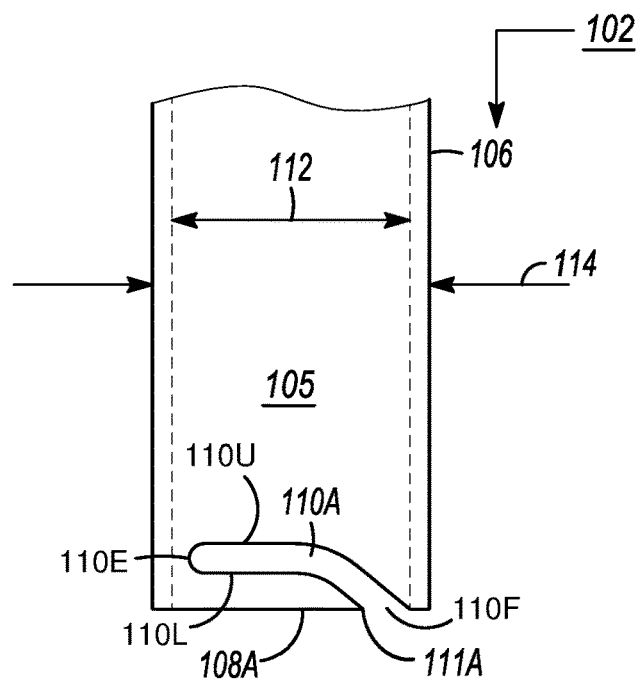

Referring to the embodiment as depicted in FIG. 12, the tine tip 111A (also called the puncturing portion) of the curved tine 108A extends downwardly (away from the curved tine 108A) so that the tine tip 111A may bite into, and puncture, the first biological wall 901 (or the pericardium layer 911). The inner diameter 112 of the catheter lumen 105 of the tissue-engaging device 106 is configured to slidably receive, and guide the movement of, the elongated puncture device 800 (as depicted in FIG. 7) toward the first surface 921 (outer surface) of the first biological wall 901 (or the pericardium layer 911). A curved tine groove 110A is formed between the curved tine 108A and the distal portion of the tissue-engaging device 106. The curved tine groove 110A includes an opening 110F adjacent the tine tip 111A and opposite closed end 110E. The curved tine groove 110A includes a first edge 110U and a second edge 110L, both extending between the opening 110F and the closed end 110E. The first edge 110U and the second edge 110L are parallel to one another along the entire length of the curved tine groove 110A from the opening 110F to the closed end 110E. The second edge 110L is defined by the top surface of the curved tine 108A. As such, first edge 110U and the second edge 110L include portions that are flat and parallel to the first biological wall 901 when pulling back the first biological wall 901. The curved tine groove 110A is configured to receive (at least in part) a portion of the first biological wall 901 (or the pericardium layer 911), once or after the first biological wall 901 (or the pericardium layer 911) is punctured. The tine tip 111A extends from the distal portion of the curved tine 108A. The outer diameter 114 is the size of the hole to be punctured through the first biological wall 901 (or the pericardium layer 911). The thickness (depth) of the curved tines (108A, 108B) may be configured for a desired target anatomy. For instance, for the pericardium layer 911, the thickness (depth) of the curved tines (108A, 108B) is from about 0.5 to about 1.5 millimeters (mm). The inner diameter 112 of the tissue-engaging device 106 may be sufficient to allow passage of a guidewire or puncture device, etc. The outer diameter 114 may be large enough to provide device integrity and/or torque transfer, while remaining small enough to track easily towards the first biological wall 901 (or the pericardium layer 911).

Figure 13:
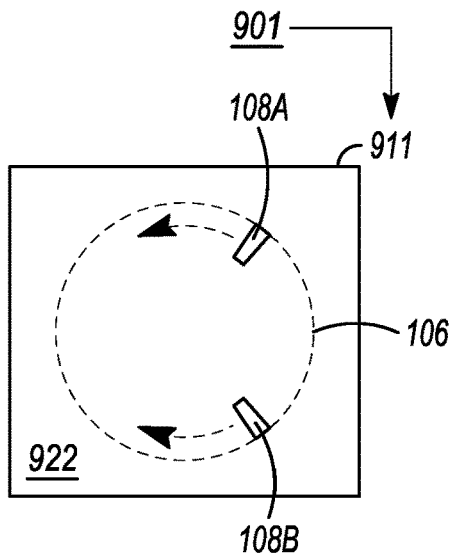

Referring to the embodiment as depicted in FIG. 13, the first biological wall 901 (or the pericardium layer 911) has been initially punctured (at the puncture site 122, also indicated in FIG. 13) by the tine tips (111A, 111B), also called the puncturing portions, of the curved tines (108A, 108B). After the first biological wall 901 (or the pericardium layer 911) becomes punctured by the tine tips (111A, 111B), and the curved tines (108A, 108B) are rotated (twisted) along a rotational direction (as indicated in FIG. 13); in this manner, the tine tips (111A, 111B) are twisted (screwed) for rotational movement (curved movement or travel) along (that is, twisted into) the first biological wall 901.

Figure 14:
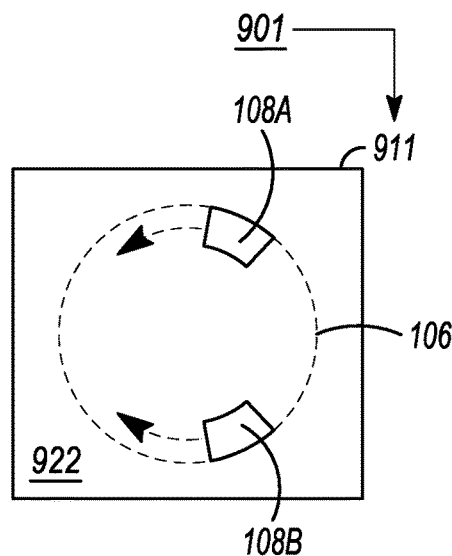

Referring to the embodiment as depicted in FIG. 14 (showing a bottom view), the first biological wall 901 (or the pericardium layer 911) has been punctured (at the puncture site 122, also indicated in FIG. 13) by the tine tips (111A, 111B), also called the puncturing portions, of the curved tines (108A, 108B). After the first biological wall 901 (or the pericardium layer 911) has been punctured (by the tine tips (111A, 111B)), the curved tines (108A, 108B) continue to be rotated (twisted) along the rotational direction (as indicated in FIG. 14), thereby urging rotational movement (curved movement or travel) of the tine tips (111A, 111B) along the second surface 922 of the second biological wall 902 (or the myocardium layer 912). The movement (curved or rotational movement) of the curved tines (108A, 108B), in turn, urges continued rotational (twisted) movement of the curved tines (108A, 108B) and the tine tips (111A, 111B) along a curved path extending along the second surface 922 (also called the inner layer) of the first biological wall 901 (or the pericardium layer 911) to the position as indicated in FIG. 14. In this manner, a length (a curved length) of the curved tines (108A, 108B), in use, may contact (engage) a section or portion of the second surface 922 of the first biological wall 901 (or the pericardium layer 911) as indicated in FIG. 14.

Figure 15:
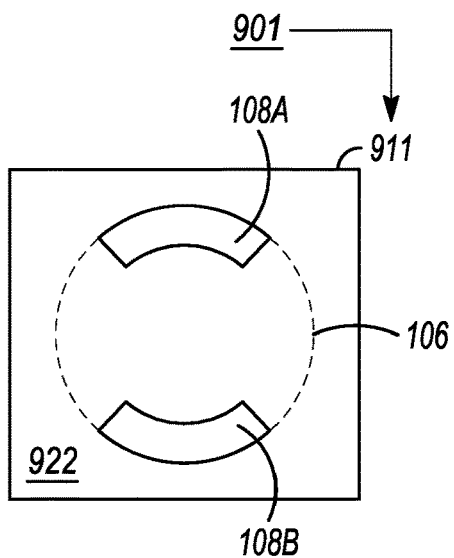

Referring to the embodiment as depicted in FIG. 15 (showing a bottom view), the first biological wall 901 (or the pericardium layer 911) has been punctured (at the puncture site 122, also indicated in FIG. 13) by the tine tips (111A, 111B), also called the puncturing portions, of the curved tines (108A, 108B). After the first biological wall 901 (or the pericardium layer 911) has been punctured (by the tine tips (111A, 111B)), the curved tines (108A, 108B) are rotated (twisted) along the rotational direction (as indicated in FIG. 13), thereby urging rotational movement (curved movement or travel) of the tine tips (111A, 111B) along the second surface 922 of the second biological wall 902 (or the myocardium layer 912). The first surface 921 (the outer surface) of the first biological wall 901 faces (the outer wall of) the second biological wall 902 (as indicated in FIG. 6). The movement (curved or rotational movement) of the curved tines (108A, 108B), in turn, urges rotational (twisted) movement of the curved tines (108A, 108B) and the tine tips (111A, 111B) along a curved path extending along the second surface 922 (also called the inner layer) of the first biological wall 901 (or the pericardium layer 911) to the position as indicated in FIG. 13. In this manner, a length (a curved length) of the curved tines (108A, 108B), in use, may contact (engage) a section or portion of the second surface 922 of the first biological wall 901 (or the pericardium layer 911) as indicated in FIG. 15. Once or after the curved tines (108A, 108B) are positioned (as depicted in FIG. 15), the tissue-engaging device 106, along with the curved tines (108A, 108B), may be retracted (or moved away from) the second biological wall 902 (or the myocardium layer 912), as depicted in FIG. 6; in this manner, retracted movement of the tissue-engaging device 106, along with the curved tines (108A, 108B) positioned as depicted in FIG. 15, urges stretching of the first biological wall 901 (or the pericardium layer 911) away from the second biological wall 902 (or the myocardium layer 912), as depicted in FIG. 6. Therefore, in response to retracted movement of the tissue-engaging device 106 along with the curved tines (108A, 108B) while the curved tines (108A, 108B) remain in contact with the second surface 922 (as depicted in FIG. 15), the first biological wall 901 (or the pericardium layer 911) becomes stretched away from the second biological wall 902 (or the myocardium layer 912, as indicated in FIG. 6), and then the elongated puncture device 800 may be deployed for the formation of the puncture passage 900 (that extends through the first biological wall 901, or the pericardium layer 911, but without inflicting damage to the second biological wall 902, as depicted in FIG. 7).

Referring to the embodiments as depicted in FIG. 13 and FIG. 14, the tissue-engaging device 106 is also configured to be selectively urged to contact, at least in part, a second surface 922 (the inner surface) of the first biological wall 901 after the tissue-engaging device 106 has punctured through the first biological wall 901; this is done, preferably, in such a way that the tissue-engaging device 106, in use, elastically stretches a section of the first biological wall 901 away from the second biological wall 902 in response to the tissue-engaging device 106 being urged to move away from the second biological wall 902.

Referring to the embodiments as depicted in FIG. 13 an FIG. 14, the second surface 922 of the first biological wall 901 (which is contacted by or touches, the tissue-engaging device 106 after the tissue-engaging device 106 has been urged to further move and further contact, at least in part, the second surface 922 of the first biological wall 901) includes an elongated area contacting the tissue-engaging device 106.

FIG. 16 to FIG. 19 depict a perspective view (FIG. 16), a side view (FIG. 17) and bottom views (FIG. 18 and FIG. 19) of embodiments of the tissue-engaging device 106 of FIG. 3.

Figure 16:
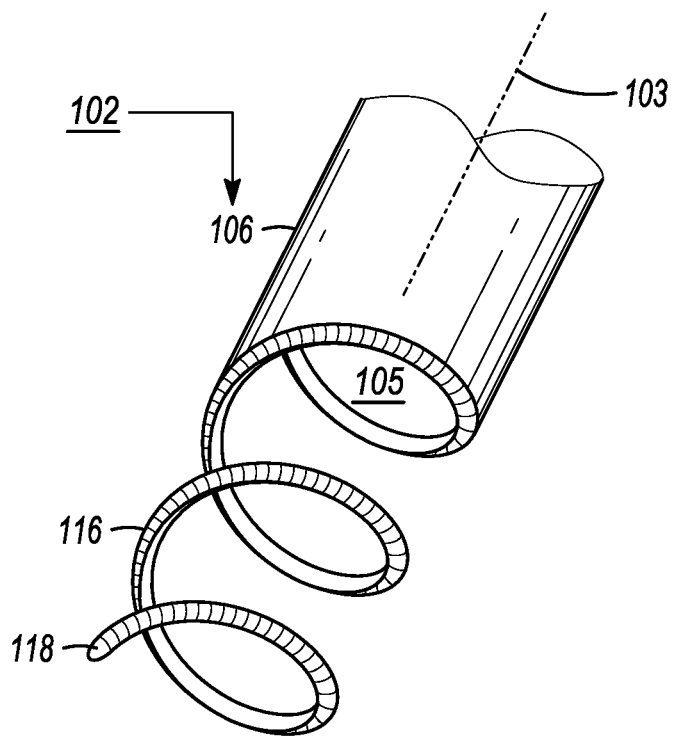
FIG. 16 to FIG. 19 depict a perspective view (FIG. 16), a side view (FIG. 17) and bottom views (FIG. 18 and FIG. 19) of embodiments of the tissue-engaging device of FIG. 3.

Referring to the embodiment as depicted in FIG. 16 (depicting a perspective view), the tissue-engaging device 106 of the elongated catheter 102 has the longitudinal axis 103 extending axially along the tissue-engaging device 106. The tissue-engaging device 106 of the elongated catheter 102 defines the catheter lumen 105 configured to slidably receive, and guide the movement of, the elongated puncture device 800 (as depicted in FIG. 7). The tissue-engaging device 106 includes a spiral formation 116 presents a spiral tip 118. The spiral tip 118 is configured to puncture the first biological wall 901 in response to rotation of the tissue-engaging device 106 after the tissue-engaging device 106 is moved to contact the first biological wall 901. The spiral formation 116 includes a spiral spacing 120 configured to receive, at least in part, a portion of the first biological wall 901 after the first biological wall 901 (or the pericardium layer 911) is punctured by the spiral tip 118. The tissue-engaging device 106 of the elongated catheter 102 has the longitudinal axis 103 extending axially along the tissue-engaging device 106. In accordance with an embodiment, the tissue-engaging device 106 and/or the elongated catheter 102 include(s) a hypotube. The tissue-engaging device 106 of the elongated catheter 102 defines the catheter lumen 105 configured to slidably receive, and guide the movement of, the elongated puncture device 800 (as depicted in FIG. 7). The spiral formation 116 (threaded formation) forms at least one winding extending in a continuous and/or a curved formation, a gradually widening tightening formation or a gradually tightening curved formation, either around a central point on a flat plane or about an axis so as to form a cone, etc., a spiral spacing 120 between the curved loops of the curved formation. The spiral spacing 120 is configured to receive (at least in part) a portion of the first biological wall 901 (or the pericardium layer 911) once the first biological wall 901 (or the pericardium layer 911) is punctured. The spiral tip 118 extends from the portion of the spiral formation 116. The tissue-engaging device 106 has an inner diameter 112 and an outer diameter 114.

Figure 17:
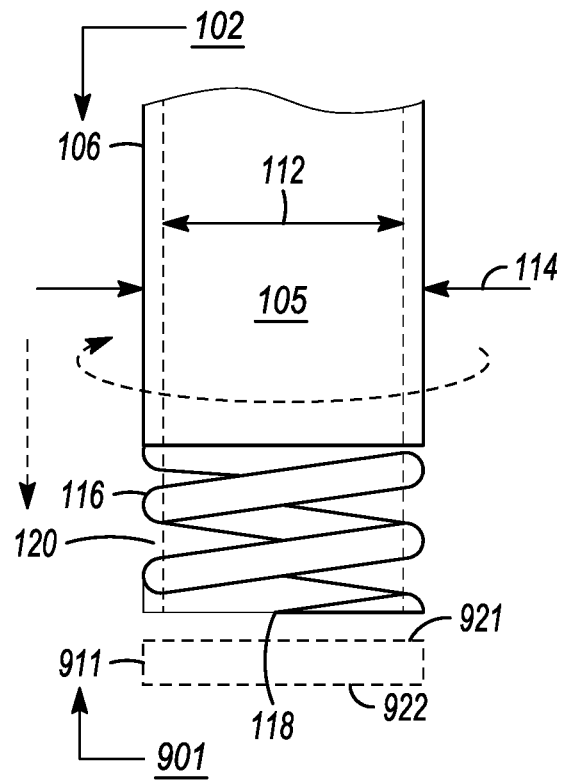

Referring to the embodiment as depicted in FIG. 17 (depicting a side view), the spiral tip 118 (also called the puncturing portion) of the spiral formation 116 is positioned proximate to (for contacting) the first surface 921 (outer surface) of the first biological wall 901 (or the pericardium layer 911). Puncturing of the first biological wall 901 (or the pericardium layer 911) by the spiral tip 118 is to be performed in response to movement (curved or rotational movement) of the tissue-engaging device 106 along with translation (linear movement) of the tissue-engaging device 106 further toward the first biological wall 901 (or the pericardium layer 911); in this manner, the spiral formation 116 may auger (rotationally urge) the spiral tip 118 through the first biological wall 901 (or the pericardium layer 911), from the first surface 921 (outer surface) to the second surface 922 (inner surface). Rotational movement of the tissue-engaging device 106 is configured to urge rotational (twisted) movement of the spiral formation 116 and the spiral tip 118 into the first biological wall 901 (or the pericardium layer 911). The inner diameter 112 is configured to slidably receive, and guide the movement of, the elongated puncture device 800 (as depicted in FIG. 7) toward the first surface 921 of the first biological wall 901 (or the pericardium layer 911).

Figure 18:
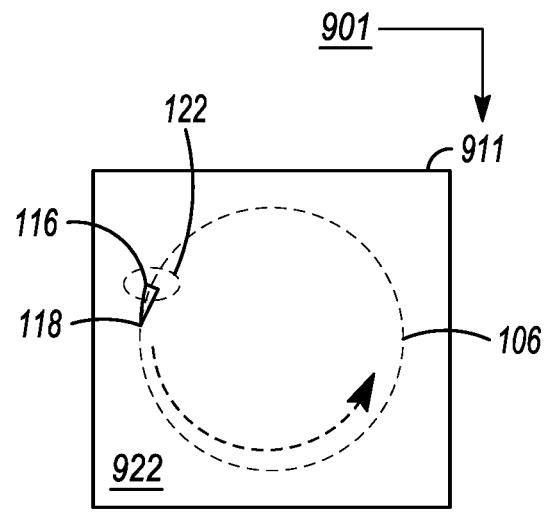

Referring to the embodiment as depicted in FIG. 18, (showing a bottom view of FIG. 17), the first biological wall 901 (or the pericardium layer 911) has been initially punctured (at the puncture site 122) by the spiral tip 118 (also called the puncturing portion) of the spiral formation 116. Puncturing of the first biological wall 901 (or the pericardium layer 911) by the spiral tip 118 is performed in response to movement (curved or rotational movement) of the tissue-engaging device 106 along with translation (linear movement) of the tissue-engaging device 106 further toward the first biological wall 901 (or the pericardium layer 911); in this manner, the spiral formation 116 may auger (rotationally urge) the spiral tip 118 through the first biological wall 901 (or the pericardium layer 911), from the first surface 921 (outer surface) to the second surface 922 (inner surface), as depicted in FIG. 17. Rotational movement of the tissue-engaging device 106 urges rotational (twisted) movement of the spiral formation 116 and the spiral tip 118 into the first biological wall 901 (or the pericardium layer 911). After the first biological wall 901 (or the pericardium layer 911) has been punctured (by the spiral tip 118), the spiral formation 116 may be further rotated (twisted) along the rotational direction as indicated in FIG. 18), thereby urging rotational movement (curved movement or travel) of the spiral tip 118 along the second surface 922 of the second biological wall 902 (or the pericardium layer 911).

Figure 19:
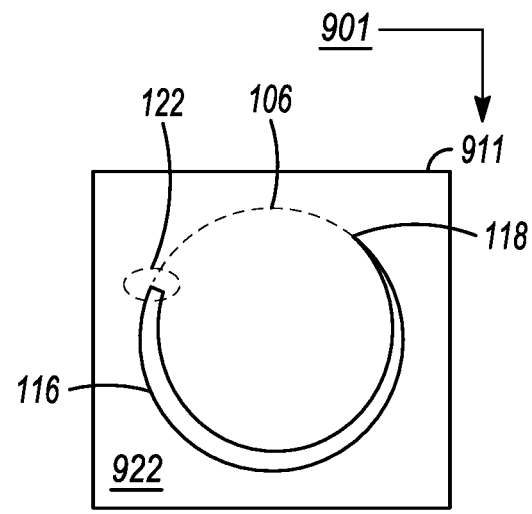

Referring to the embodiment as depicted in FIG. 19 (showing a bottom view of FIG. 17), the first biological wall 901 (or the pericardium layer 911) has been punctured (at the puncture site 122, also indicated in FIG. 18) by the spiral tip 118 (also called the puncturing portion) of the spiral formation 116. After the first biological wall 901 (or the pericardium layer 911) has been punctured (by the spiral tip 118), the spiral formation 116 is rotated (twisted) along the rotational direction (as depicted in FIG. 18), thereby urging rotational movement (curved movement or travel) of the spiral tip 118 along the second surface 922 of the second biological wall 902 (or the myocardium layer 912). The first surface 921 (the outer layer) of the first biological wall 901 faces (the outer wall of) the second biological wall 902 (as indicated in FIG. 6). The movement (curved or rotational movement) of the spiral formation 116, in turn, urges rotational (twisted) movement of the spiral tip 118 along a curved path extending along the second surface 922 (also called the inner layer) of the first biological wall 901 (or the pericardium layer 911) to the position as indicated in FIG. 19. In this manner, a length (a curved length) of the spiral formation 116, in use, may contact (engage) a section or portion of the second surface 922 of the first biological wall 901 (or the pericardium layer 911) as indicated in FIG. 19. Once or after the spiral formation 116 is positioned (as depicted in FIG. 19), the tissue-engaging device 106 (along with the spiral formation 116) may be retracted (or moved away from) the second biological wall 902 (or the myocardium layer 912), as depicted in FIG. 6; in this manner, retracted movement of the tissue-engaging device 106 (along with the spiral formation 116 positioned, as depicted in FIG. 19) urges stretching of the first biological wall 901 (or the pericardium layer 911) away from the second biological wall 902 (or the myocardium layer 912), as depicted in FIG. 6. Therefore, in response to retracted movement of the tissue-engaging device 106 along with the spiral formation 116 while the spiral formation 116 remains in contact with the second surface 922 (as depicted in FIG. 19), the first biological wall 901 (or the pericardium layer 911) becomes stretched away from the second biological wall 902 (or the myocardium layer 912, as indicated in FIG. 6); then the elongated puncture device 800 may be deployed for the formation of the puncture passage 900 (that extends through the first biological wall 901, or the pericardium layer 911, but without inflicting damage to the second biological wall 902, as depicted in FIG. 7).

Referring to the embodiments as depicted in FIG. 18 and FIG. 19, the tissue-engaging device 106 is also configured to be selectively urged to contact, at least in part, a second surface 922 (the inner surface) of the first biological wall 901 after the tissue-engaging device 106 has punctured through the first biological wall 901; this is done, preferably, in such a way that the tissue-engaging device 106, in use, elastically stretches a section of the first biological wall 901 away from the second biological wall 902 in response to the tissue-engaging device 106 being urged to move away from the second biological wall 902.

Referring to the embodiments as depicted in FIG. 18 and FIG. 19, the second surface 922 of the first biological wall 901 (which is contacted by the tissue-engaging device 106 after the tissue-engaging device 106 has been urged to further move and further contact, at least in part, the second surface 922 of the first biological wall 901) includes an elongated area contacting the tissue-engaging device 106.

In view of the foregoing descriptions, it will be appreciated that the tissue-engaging device 106 may reach the first pericardial layer from the skin; that is, the tissue-engaging device 106 may be fitted with a stylet or needle, and then may be advanced through an access site at the skin of the patient. It will be understood that this aspect is appreciated by the FIGS. and/or the above description. The leading edge of tissue-engaging device 106 may be configured as to mitigate damage to the tissue-engaging device 106 and/or the fascia and/or surrounding tissue as the tissue-engaging device 106 is advanced mechanically. In other embodiments, the tissue-engaging device 106 is advanced through a previously inserted sheath, or embodied with an integrated shroud, etc.

In view of the foregoing descriptions, it will be appreciated that the tissue-engaging device 106 may be compatible with injection of a contrast fluid (to confirm tissue stretching/capture). It will be appreciated that the tissue-engaging device 106 may be configured to reduce potential of unwanted injury resulting from pressure (i.e. the user may utilize EGMs to confirm how much force is applied prior to rotational capturing of the primary wall by the tissue-engaging device 106). It will be appreciated that the tissue-engaging device 106 may be integrated with a medical map for the case where the tissue-engaging device 106 is conductive with an electrically insulted body extending to the tip (distal tip); this is done for visualization of the tissue-engaging device 106 via an electroanatomical medical imaging system (EAM), on that basis that it may be helpful to approximate location of tip of the tissue-engaging device 106 before attempting tissue capture. It will be appreciated that the tissue-engaging device 106 may used with a transseptal puncture device with a torquable, flexible tube that extends to the septum via a guide catheter, etc. It will be appreciated that the tissue-engaging device 106 may be used with a bovie device (an instrument used for electrosurgical dissection and hemostasis) by energizing a rotational mechanism to cut the pericardium, and may (during usage of the transseptal puncture device) also provide controlled septostomy, etc.

The following is offered as further description of the embodiments, in which any one or more of any technical feature (described in the detailed description, the summary and the claims) may be combinable with any other one or more of any technical feature (described in the detailed description, the summary and the claims). It is understood that each claim in the claims section is an open ended claim unless stated otherwise. Unless otherwise specified, relational terms used in these specifications should be construed to include certain tolerances that the person skilled in the art would recognize as providing equivalent functionality. By way of example, the term perpendicular is not necessarily limited to 90.0 degrees, and may include a variation thereof that the person skilled in the art would recognize as providing equivalent functionality for the purposes described for the relevant member or element. Terms such as "about" and "substantially", in the context of configuration, relate generally to disposition, location, or configuration that are either exact or sufficiently close to the location, disposition, or configuration of the relevant element to preserve operability of the element within the disclosure which does not materially modify the disclosure. Similarly, unless specifically made clear from its context, numerical values should be construed to include certain tolerances that the person skilled in the art would recognize as having negligible importance as they do not materially change the operability of the disclosure. It will be appreciated that the description and/or drawings identify and describe embodiments of the apparatus (either explicitly or inherently). The apparatus may include any suitable combination and/or permutation of the technical features as identified in the detailed description, as may be required and/or desired to suit a particular technical purpose and/or technical function. It will be appreciated that, where possible and suitable, any one or more of the technical features of the apparatus may be combined with any other one or more of the technical features of the apparatus (in any combination and/or permutation). It will be appreciated that persons skilled in the art would know that the technical features of each embodiment may be deployed (where possible) in other embodiments even if not expressly stated as such above. It will be appreciated that persons skilled in the art would know that other options may be possible for the configuration of the components of the apparatus to adjust to manufacturing requirements and still remain within the scope as described in at least one or more of the claims. This written description provides embodiments, including the best mode, and also enables the person skilled in the art to make and use the embodiments. The patentable scope may be defined by the claims. The written description and/or drawings may help to understand the scope of the claims. It is believed that all the crucial aspects of the disclosed subject matter have been provided in this document. It is understood, for this document, that the word "includes" is equivalent to the word "comprising" in that both words are used to signify an open-ended listing of assemblies, components, parts, etc. The term "comprising", which is synonymous with the terms "including," "containing," or "characterized by," is inclusive or open-ended and does not exclude additional, unrecited elements or method steps. Comprising (comprised of) is an "open" phrase and allows coverage of technologies that employ additional, unrecited elements. When used in a claim, the word "comprising" is the transitory verb (transitional term) that separates the preamble of the claim from the technical features of the disclosure. The foregoing has outlined the non-limiting embodiments (examples). The description is made for particular non-limiting embodiments (examples). It is understood that the non-limiting embodiments are merely illustrative as examples.

What is claimed is:

1. An apparatus for use with a first biological wall positioned adjacent to a second biological wall of a patient, the apparatus comprising:
   an elongated catheter including a distal catheter section having a tissue-engaging device configured to be urged to move and contact a first surface of the first biological wall; and
   the tissue-engaging device extending, at least in part, from the distal catheter section, the tissue-engaging device including a first curved tine and a second curved tine positioned on opposite sides of the tissue-engaging device, the first curved tine and the second cured tine being positioned on, and extending from, a circumferential edge of the tissue-engaging device; and
   a first curved tine groove positioned between the first curved tine and a distal portion of the tissue-engagement device and a second curved tine groove positioned between the second curved tine and the distal portion of the tissue-engagement device, the first curved tine groove and the second curved tine groove each having an opening, a closed end opposite the opening, a first edge, and a second edge, wherein the first edge and the second edge are parallel from the opening to the closed end; and
   the tissue-engaging device configured to be urged to puncture through the first biological wall after the tissue-engaging device has been urged to move and contact the first surface of the first biological wall; and
   the tissue-engaging device also configured to be urged to contact, at least in part, the first surface of the first biological wall, without impinging the second biological wall, after the tissue-engaging device has punctured through the first biological wall.

2. The apparatus of claim 1, wherein:
   the tissue-engaging device is also configured to be selectively urged to contact, at least in part, a second surface of the first biological wall after the tissue-engaging device has punctured through the first biological wall in such a way that the tissue-engaging device, in use, elastically stretches a section of the first biological wall away from the second biological wall in response to the tissue-engaging device being urged to move away from the second biological wall.

3. The apparatus of claim 1, wherein:
   a second surface of the first biological wall, which is contacted by the tissue-engaging device after the tissue-engaging device has been urged to further move and further contact the second surface of the first biological wall, includes:
   an elongated area contacting the tissue-engaging device.

4. The apparatus of claim 1, wherein:
   the elongated catheter is configured to slidably guide, at least in part, movement of an elongated puncture device toward the tissue-engaging device; and
   the elongated puncture device is configured to form a puncture passage extending through the first biological wall after the elongated puncture device is slidably guided, at least in part, toward the first biological wall and past the tissue-engaging device; and
   the tissue-engaging device is also configured to be selectively urged to contact, at least in part, a portion of a second surface of the first biological wall, without impinging the second biological wall, after the tissue-engaging device is urged to puncture through the first biological wall in such a way that the tissue-engaging device, in use, elastically stretches a section of the first biological wall away from the second biological wall, in response to the tissue-engaging device being urged to move away from the second biological wall, while the elongated puncture device is moved to puncture through the portion of the first biological wall engaged by the tissue-engaging device.

5. The apparatus of claim 4, wherein the elongated puncture device is a radio frequency puncture device.

6. The apparatus of claim 1, wherein:
   the tissue-engaging device is rotatable, at least in part, about a longitudinal axis extending, at least in part, along the elongated catheter in response to rotation of the elongated catheter; and
   the tissue-engaging device is also configured to be selectively urged to rotatably contact, at least in part, a second surface of the first biological wall, without impinging the second biological wall.

7. The apparatus of claim 1, wherein:
   the tissue-engaging device is also configured to selectively disengage from the first biological wall in response to rotation of the distal catheter section about a longitudinal axis extending along the elongated catheter.

8. The apparatus of claim 1, wherein:
   the tissue-engaging device is also configured to be movable into a biological space located between the first biological wall and the second biological wall in such a way that the tissue-engaging device is spaced apart from the second biological wall without engaging the second biological wall.

9. The apparatus of claim 1, wherein:
   the elongated catheter is configured to slidably guide, at least in part, movement of an elongated puncture device toward the tissue-engaging device; and
   the elongated puncture device is configured to form a puncture passage extending through the first biological wall after the elongated puncture device is slidably guided, at least in part, toward the first biological wall and past the tissue-engaging device; and
   the tissue-engaging device is configured to maintain separation between the first biological wall and the second biological wall while the elongated puncture device is maneuvered, along the elongated catheter, and positioned to form the puncture passage extending through the first biological wall without inadvertently damaging the second biological wall.

10. The apparatus of claim 9, wherein:
the tissue-engaging device is configured to selectively engage, at least in part, the first biological wall in response to rotation of the distal catheter section to urge the tissue-engaging device to selectively engage with a second surface of the first biological wall after the tissue-engaging device has been maneuvered to contact the first biological wall.

11. The apparatus of claim 10, wherein:
a biological space is located between the first biological wall and the second biological wall; and
the tissue-engaging device is also configured to remain engaged with the first biological wall while the distal catheter section is moved away from the second biological wall thereby elastically stretching the first biological wall away from the second biological wall thereby locally enlarging the biological space that is located proximate to the tissue-engaging device.

12. The apparatus of claim 11, wherein:
the elongated catheter is configured to slidably guide, at least in part, movement of the elongated puncture device toward the tissue-engaging device; and
the elongated puncture device is configured to form the puncture passage extending through the first biological wall after the elongated puncture device is slidably guided, at least in part, toward the first biological wall and past the tissue-engaging device; and
the tissue-engaging device is also configured to maintain engagement with the first biological wall while the elongated puncture device, in use, is maneuvered along the elongated catheter toward the first biological wall via the distal catheter section, and the elongated puncture device is configured to form the puncture passage extending through the first biological wall without imparting damage to the second biological wall.

13. The apparatus of claim 1, wherein:
the elongated catheter is configured to slidably guide, at least in part, movement of an elongated puncture device toward the tissue-engaging device; and
the elongated puncture device is configured to form a puncture passage extending through the first biological wall after the elongated puncture device is slidably guided, at least in part, toward the first biological wall and past the tissue-engaging device; and
the elongated catheter defines an elongated catheter lumen extending, at least in part, along the distal catheter section; and
the elongated catheter lumen is configured to slidably receive and guide movement of the elongated puncture device for exterior extension of the elongated puncture device from the distal catheter section.

14. The apparatus of claim 1, wherein:
the first and second curved tines each includes, respectively, tine tips configured to bite into, and puncture through, the first biological wall in response to rotational movement of the tissue-engaging device.

15. An apparatus for use with a first biological wall positioned adjacent to a second biological wall of a patient, the apparatus comprising:
an elongated puncture device; and
an elongated catheter including a distal catheter section having a tissue-engaging device configured to be urged to move and contact a first surface of the first biological wall; and
the elongated catheter configured to slidably guide, at least in part, movement of the elongated puncture device toward the tissue-engaging device; and
the elongated puncture device configured to form a puncture passage extending through the first biological wall after the elongated puncture device is slidably guided, at least in part, toward the first biological wall and past the tissue-engaging device; and
the tissue-engaging device extending, at least in part, from the distal catheter section; and
the tissue-engaging device configured to be urged to puncture through the first biological wall after the tissue-engaging device has been urged to move and contact the first surface of the first biological wall; and
the tissue-engaging device also configured to be urged to contact, at least in part, the first surface of the first biological wall, without impinging the second biological wall, after the tissue-engaging device has punctured through the first biological wall; and
the tissue-engaging device also configured to be selectively urged to contact, at least in part, a second surface of the first biological wall, without impinging the second biological wall, after the tissue-engaging device is urged to puncture past the first surface and through the first biological wall in such a way that the tissue-engaging device, in use, elastically stretches, at least in part, the first biological wall away from the second biological wall in response to the tissue-engaging device being urged to move away from the second biological wall, and the elongated puncture device is movable to puncture through the first biological wall; and
wherein the tissue-engaging device includes a first curved tine and a second curved tine positioned on opposite sides of the tissue-engaging device, the first curved tine and the second cured tine being positioned on, and extending from, a circumferential edge of the tissue-engaging device; and
a first curved tine groove positioned between the first curved tine and a distal portion of the tissue-engagement device and a second curved tine groove positioned between the second curved tine and the distal portion of the tissue-engagement device, the first curved tine groove and the second curved tine groove each having an opening, a closed end opposite the opening, a first edge, and a second edge, wherein the first edge and the second edge are parallel from the opening to the closed end.

16. The apparatus of claim 15, wherein the elongated puncture device is a radio frequency puncture device.

17. An apparatus for use with a first biological wall positioned adjacent to a second biological wall of a patient, the apparatus comprising:
an elongated catheter including a distal catheter section having a tissue-engaging device configured to be urged to move and contact a first surface of the first biological wall; and
the tissue-engaging device extending, at least in part, from the distal catheter section, the tissue-engaging device consisting of:
a first curved tine and a second curved tine positioned on opposite sides of the tissue-engaging device, the first curved tine and the second cured tine being positioned on, and extending from, a circumferential edge of the tissue-engaging device; and
a first curved tine groove positioned between the first curved tine and a distal portion of the tissue-engagement device and a second curved tine groove positioned between the second curved tine and the distal portion of the tissue-engagement device, the first curved tine groove and the second curved tine groove each having an opening adjacent a tine tip, a closed end opposite the opening, a first edge, and a second edge, wherein the first edge and the second edge are parallel from the opening to the closed end.

18. The apparatus of claim 17, wherein a portion of the first edge and the second edge are parallel to the first surface of the first biological wall.

* * * * *